United States Patent
Quattropani et al.

(10) Patent No.: US 10,344,021 B2
(45) Date of Patent: Jul. 9, 2019

(54) PROCESS FOR THE SEPARATION OF ENANTIOMERS OF PIPERAZINE DERIVATIVES

(71) Applicant: Asceneuron SA, Lausanne (CH)

(72) Inventors: Anna Quattropani, Rolle (CH); Santosh S. Kulkarni, Bangalore (IN); Awadut Gajendra Giri, Bangalore (IN); Johannes Nicolaas Koek, Sauwerd (NL)

(73) Assignee: Asceneuron S A, Lausanne (CH)

( * ) Notice: Subject to any disclaimer, the term of this patent is extended or adjusted under 35 U.S.C. 154(b) by 0 days.

(21) Appl. No.: 16/078,715

(22) PCT Filed: Feb. 24, 2017

(86) PCT No.: PCT/EP2017/054272
§ 371 (c)(1),
(2) Date: Aug. 22, 2018

(87) PCT Pub. No.: WO2017/144635
PCT Pub. Date: Aug. 31, 2017

(65) Prior Publication Data
US 2019/0062316 A1    Feb. 28, 2019

(30) Foreign Application Priority Data

Feb. 25, 2016    (IN) .............................. 201621006637

(51) Int. Cl.
*C07D 405/06* (2006.01)
*C07B 57/00* (2006.01)

(52) U.S. Cl.
CPC ............ *C07D 405/06* (2013.01); *C07B 57/00* (2013.01); *C07B 2200/07* (2013.01)

(58) Field of Classification Search
CPC .................................................. C07D 405/06

USPC .......................................................... 544/359
See application file for complete search history.

(56) References Cited

FOREIGN PATENT DOCUMENTS

| FR | 1 311 316 A | 12/1962 |
| WO | WO 2014/159234 A1 | 10/2014 |
| WO | WO 2016/030443 A1 | 3/2016 |

OTHER PUBLICATIONS

Collet A. "Resolution of Racemates: Did you say 'Classical?'", Angewandte Chemie International Edition, vol. 37, No. 23, 1998, pp. 3239-3241.
Database accession No. 54914491; Jan. 24, 2012; 13 pages.
Database accession No. 28798635; May 28, 2009; 11 pages.
Database accession No. 2055841-81-9; Jan. 11, 2017; 1 page.
Database accession No. 118902929; Apr. 9, 2016, 13 pages.
Tan H. et al. "Rational Screening Approach for Classical Chiral Resolution under Thermodynamic Equilibrium: A Case Study of Diphenyl-Substituted N-Methyl-Piperazine", Organic Process Research and Development, vol. 15, No. 1, 2011, pp. 53-63.

*Primary Examiner* — Jeffrey H Murray
(74) *Attorney, Agent, or Firm* — Cooley LLP; Ivor R. Elrifi; Thomas J. Paxton

(57) ABSTRACT

The invention relates to a process for preparing either enantiomer of a compound of formula (I), wherein X, Y and n have the meaning given in claim 1, with high enantiomeric excess (e.e.), by chiral resolution in the presence of a non-racemic, chiral acid.

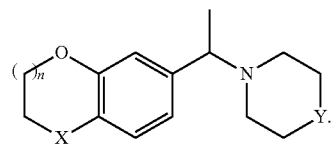

(I)

20 Claims, No Drawings

PROCESS FOR THE SEPARATION OF ENANTIOMERS OF PIPERAZINE DERIVATIVES

RELATED APPLICATIONS

This application is a U.S. National Phase application, filed under 35 U.S.C. § 371(c), of International Application No. PCT/EP2017/054272, filed Feb. 24, 2017, which claims priority to, and the benefit of, Indian Patent Application No. 201621006637, filed Feb. 25, 2016, each of which is incorporated by reference herein in its entirety for all purposes.

FIELD OF THE INVENTION

The invention relates to a process for preparing either enantiomer of piperazine derivatives, and to enantiomerically pure or enriched piperazine derivatives by chiral resolution in the presence of a non-racemic, chiral acid.

BACKGROUND OF THE INVENTION

The invention relates particularly to a process for preparing either enantiomer of a compound of formula I:

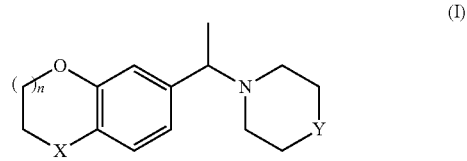

(I)

wherein
X denotes O or CH$_2$,
Y is NH or N-PG,
PG denotes a protective group
and
n denotes 0 or 1,
from the racemate of formula I or other mixtures of the enantiomers of formula I, with high enantiomeric excess (e.e.), by chiral resolution in the presence of a non-racemic, chiral acid.

Enantiomers of compounds of formula I are useful as drugs or building blocks for the synthesis of drugs, such as but not limited to glycosidase inhibitors.

For example, PCT/EP2015/069598 describes e.g. N-(5-{4-[(1S)-1-(2,3-dihydro-1-benzofuran-6-yl)ethyl]piperazin-1-yl}-1,3,4-thiadiazol-2-yl)acetamide and N-(2-{4-[(1S)-1-(2H-1,3-benzodioxol-5-yl)ethyl]piperazin-1-yl}pyrimidin-5-yl)acetamide as active glycosidase inhibitors having high inhibitory activities.

There is a need to identify the conditions and solvent systems in combination with chiral acids that can be employed reliably in processes that provide efficient resolution of the racemate of formula I.

SUMMARY

In one aspect, the present application provides processes for the preparation of either enantiomer of compounds of formula I above and in particular (S)-1-(1-(benzo[d][1,3]dioxol-5-yl)ethyl)piperazine, with high enantiomeric excess (e.e.), preferably with >95% e.e. or >98% e.e., comprising the selective crystallization of the respective racemic compound of formula I in the presence of a chiral acid yielding the crystallization of a strongly enantiomerically enriched salt form and leaving in solution the majority of the other enantiomer as a salt. After isolation of the crystalline matter, the free base of each of the respective entantiomers can be obtained by e.g. aqueous basic treatment and extraction from aqueous phase with suitable solvents, as further described below.

DETAILED DESCRIPTION

Racemic compounds of formula I:

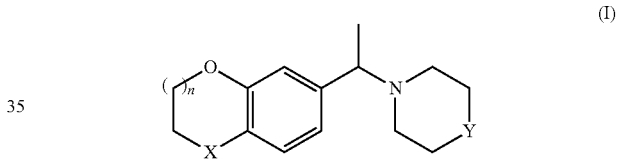

(I)

wherein
X denotes O or CH$_2$,
Y is NH or N-PG,
PG denotes a protective group
and
n denotes 0 or 1,
that are used in the chiral resolution process of the present invention, can be obtained e.g. according to Scheme 1.

Scheme 1

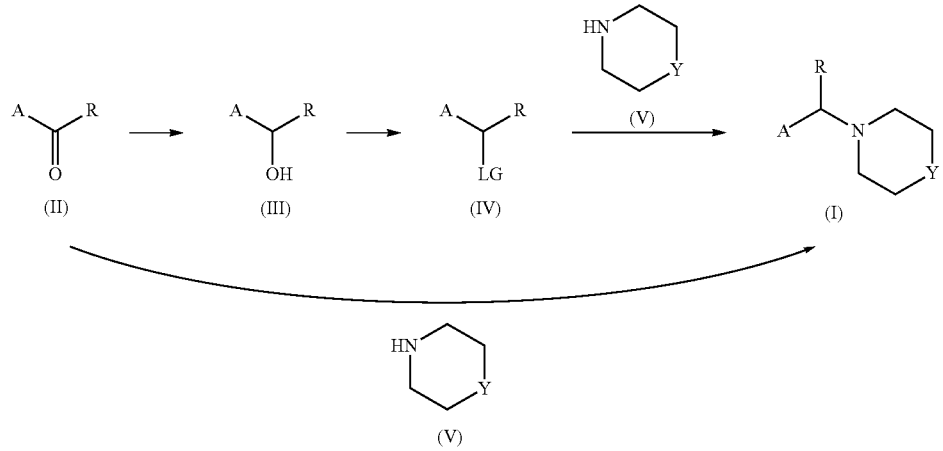

wherein
A denotes the group

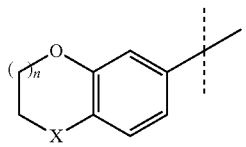

X, Y and n are as defined above. Thus, the compounds can be prepared from the corresponding ketone (II) by reductive amination with amine (V), using conditions known to the one skilled in the art, such as but not limited to the use of $NaBH(OAc)_3$ as reducing agent, in the presence of one equivalent of AcOH in DCE. Alternatively, reductive amination can be performed in two steps, with first imine formation, that can be catalysed by $Ti(OiPr)_4$, followed by reduction with suitable reducing agent, such as but not limited to $NaBH_4$ in MeOH (Abdel-Magid, A. F. at al. *J. Org. Chem.* 1996, 61, 3849-3862). Alternatively, ketone (II) can be reduced into the corresponding alcohol (III) using usual reductive agents such as $NaBH_4$ in an alcoholic solvent, such as MeOH. Alcohol functionality can be then transformed into a suitable leaving group LG, such as but not limited to Cl or OMs, using conditions known to a person skilled in the art. The addition of amine (V) to intermediate (IV) would yield the formation of compound (I). Compounds of formula I, wherein Y is NH can be obtained by removal of the group PG of compounds of formula I, wherein Y is N-PG, under standard conditions known to those skilled in the art.

A "leaving group" LG denotes a chemical moiety, which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition $SO_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

PG denotes a protecting group, which is compatible with the chemistry described above, such as but not limited to BOC (tert-butoxy-carbonyl), or $SO_2$Tol (toluolsulfonate). It can be removed under acidic conditions, such as but not limited to HCl in MeOH or dioxane or TFA in DCM for e.g. the BOO protecting group. Alternatively, a mixture of HBr, AcOH and 4-hydroxybenzoic acid or a mixture of H2SO4 and trifluoroacetic acid at temperatures ranging from RT to 100° C. can be used to cleave a sulfonamide protecting group, such as para-toluene sulfonamide. The removal of the protecting group PG yields the corresponding amine.

Preferred groups PG are the following: Carbobenzyloxy (Cbz), p-Methoxybenzyl carbonyl (Moz or MeOZ) group, tert-Butyloxycarbonyl (BOC) group, 9-Fluorenylmethyloxycarbonyl (FMOC) group, Alkanoyl group, such as the Acetyl (Ac) group, Benzoyl (Bz) group, Benzyl (Bn) group, Carbamate group, p-Methoxybenzyl (PMB), 4-Dimethoxybenzyl (DMPM), p-methoxyphenyl (PMP) group, Arylsulfonyl group such as the Tosyl (Ts) or benzolsulfonyl group.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

In certain embodiments of the present invention, Yin compounds of formula I also denotes N-Q, wherein Q is a group selected from

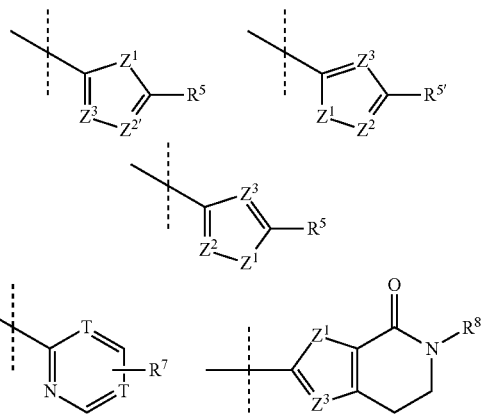

$Z^1$ is S, O, $NR^3$;

$Z^2$, $Z^{2'}$, $Z^3$ independently denote $CR^5$, $CR^6$ or N;

$R^5$, $R^{5'}$, $R^6$, $R^7$ independently denote H, Hal, $NR^3R^4$, $NO_2$, straight chain or branched alkyl having 1 to 12 carbon atoms, wherein 1 to 3 $CH_2$-groups may be replaced by a group selected from O, $NR^3$, S, SO, $SO_2$, CO, COO, OCO, $CONR^3$, $NR^3CO$ and wherein 1 to 5 hydrogen atoms may be replaced by Hal, $NR^3R^4$, $NO_2$, $OR^3$, Het, Ar, Cyc, or denote Ar, Het or Cyc;

$R^8$ denotes H, methyl or straight chain or branched alkyl having 2 to 12 carbon atoms, wherein 1 to 3 $CH_2$-groups may be replaced by a group selected from O, $NR^3$, S, SO, $SO_2$, CO, COO, OCO, $CONR^3$, $NR^3CO$ and wherein 1 to 5 hydrogen atoms may be replaced by Hal, $NR^3R^4$ or $NO_2$;

$R^3$, $R^4$ denote each independently H or a straight chain or branched alkyl group having 1 to 12 carbon atoms;

Hal denotes F, Cl, Br or I;

Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from $R^5$, Hal and $OR^3$;

Ar denotes a 6-membered carbocyclic aromatic ring or a fused or non fused bicylic aromatic ring system, which is optionally substituted by 1 to 3 substituents independently selected from $R^5$, $OR^3$ and Hal;

Cyc denotes a saturated or an unsaturated carbocyclic ring having from 3 to 8 carbon atoms which is optionally substituted by 1 to 3 substituents independently selected from $R^5$ or Hal or OH.

In further embodiments of the invention, Q is selected from the group

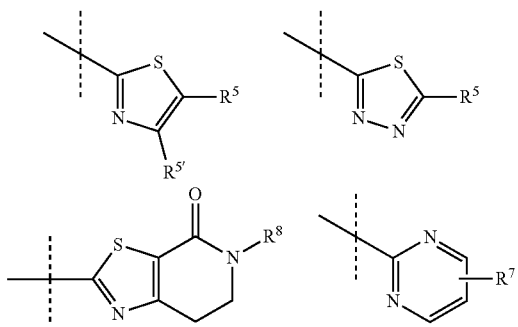

wherein R⁵, R⁵', R⁷ and R⁸ have the meaning given above.

In a preferred embodiment, the invention relates to acid addition salts of compounds of formula I or Ia, wherein $R^5$, $R^{5'}$, $R^6$, $R^7$ are independently H, Hal, $NR_3R_4$, $NH_2$, $N(CH_3)_2$, phenyl, 2-,3- or 4-hydroxy or methoxyphenyl, alkyl, $CF_3$, alkoxy (Oalkyl), hydroxyalkylen, alkoxyalkylen, COOH, COOalkyl, CONHalkyl, $CONH_2$, $CON(CH_3)_2$, NHCOalkyl, NHalkyl, CO—N-morpholinyl, $CON(CH_3)CH_2CH_2N(CH_3)_2$, CO-1-piperidinyl, CO-4-hydroxy-1-piperidinyl, CO-1-piperazinyl, CO-4-methyl-1-piperazinyl, $CH_2$—N-morpholinyl, $CH_2N(H)COCH_3$, $CH_2N(CH_3)COCH_3$, substituted or unsubstituted Cyc or Het, as well as solid forms, such as polymorphic forms, thereof.

In further preferred embodiments of the invention, Q is selected from the group:

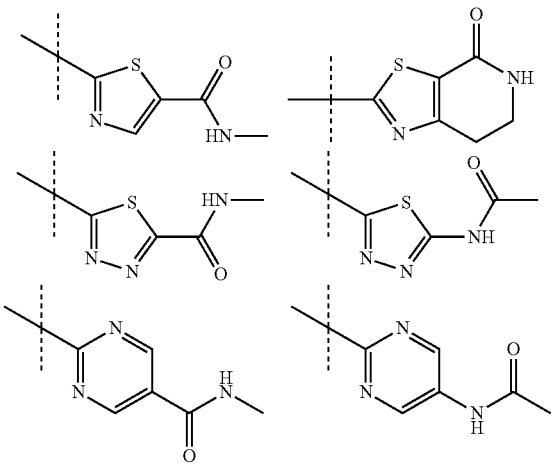

The method of the present invention can e.g. be used for the preparation of the following compounds from their corresponding racemates or by synthesis using intermediates that are obtained in enantiomerically enriched or pure form according to the process of the present invention:

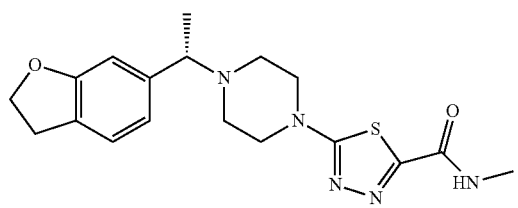

-continued

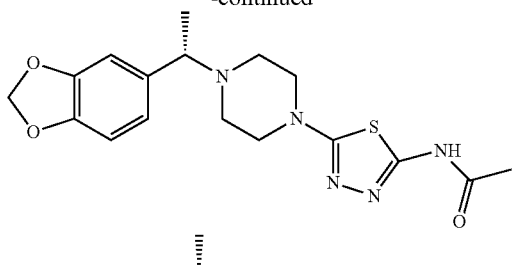

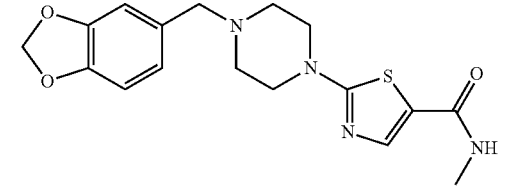

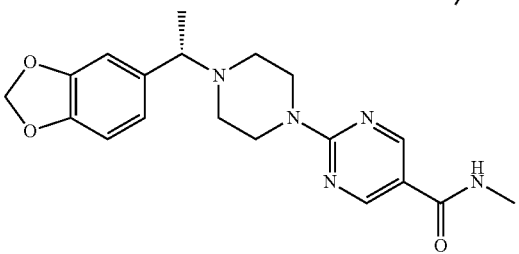

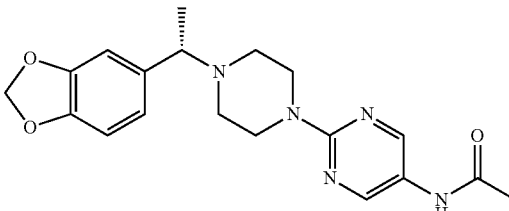

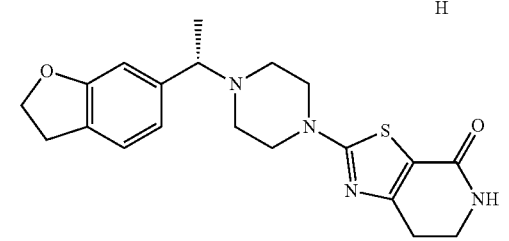

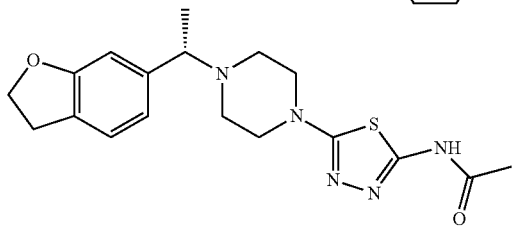

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls.

Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In an embodiment of the invention, alkyl denotes unbranched or branched alkyl having 1-10 C atoms, in which 1-7 H atoms may be replaced independently from one another by Hal. A preferred embodiment of alkyl denotes unbranched or branched alkyl having 1-6 C atoms, in which 1-4 atoms may be replaced independently from one another by Hal. In a more preferred embodiment of the invention, alkyl denotes unbranched or branched alkyl having 1-4 C atoms, in which 1-3 H atoms can be replaced independently from one another by Hal, particularly by F and/or Cl. It is most preferred that alkyl denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of alkyl is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "Ar" "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Aryl is preferably selected from the following group: phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazoM-, -4- or -5-yl, 1,2,4-triazo-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5indolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl. The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-di-hydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes piperidinyl, 4-hydroxypiperidinyl, piperazinyl, 4-methylpiperazinyl, pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

Formula I embraces the mixture of the respective enantiomers, preferably the racemic mixture of the respective enantiomers.

Enantiomers of compounds of formula I, and the S-enantiomers in particular, are useful drugs or building blocks for the synthesis of drugs, such as but not limited to glycosidase inhibitors.

The present invention provides conditions and solvent systems in combination with chiral acids that can be reliably employed in processes that provide efficient resolution of the racemate or other enantiomeric mixtures of formula Thus, in one aspect, the invention relates to a process for preparing either enantiomer of a compound of formula I:

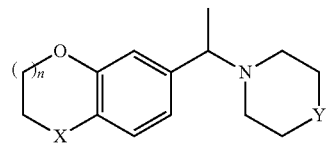

(I)

wherein
X denotes O or $CH_2$,
Y is NH or N-PG,
PG denotes a protective group
and
n denotes 0 or 1,
with high enantiomeric excess (e.e.), preferably with >95% e.e. or >98% e.e., comprising the selective crystallization of the respective racemic compound of formula I or other mixtures of the enantiomers of formula I in the presence of a chiral, non-racemic acid yielding the crystallization of a strongly enantiomerically enriched solid salt form and leaving in solution the majority of the other enantiomer as a salt. After isolation of the crystalline matter, the free base of each of the respective entantiomers can be obtained by e.g. aqueous basic treatment and extraction from aqueous phase with suitable solvents.

The method of the invention is particularly useful to prepare compounds of foruma II, i.e the S-enantiomers of formula I:

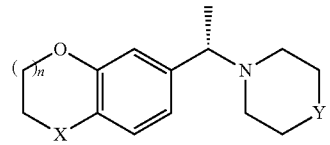

(II)

wherein X, n and Y are as defined above or the corresponding R-enantiomer.

Thus, the present invention relates to a process for the separation of the enantiomers of a compound of formula I, comprising the steps of:

a) contacting the respective racemate or other enantiomeric mixture of the respective compound of formula I with a chiral, non-racemic acid in a suitable solvent, b) optionally heating the mixture obtained under step a) from about 30° C. to about 120° C., such as between 40° C. and 100° C. or between 45° C. and 80° C. or heating the mixture to the boiling point of the selected solvent and allowing the mixture to cool to room temperature;

c) separating the formed crystals from the solution; and d) optionally liberating the free base of the respective enantiomer of formula I from the formed crystals obtained under c) by treatment with a base.

n is preferably 0.

A very preferred racemate or other enantiomeric mixture of a compound of formula I is the compound of formula (I') (1-(1-(benzo[d][1,3]dioxol-5-yl)ethyl)piperazine), and preferably its racemate:

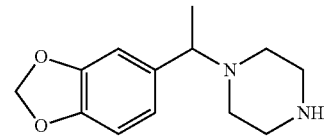

(I')

In one aspect the present application specifically relates to a process for preparing (S)-1-(1-(benzo[d][1,3]dioxol-5-yl)ethyl)piperazine of formula (Ib')

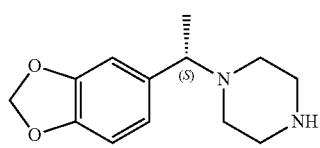

(Ib')

with high enantiomeric excess (e.e.), preferably with >95% e.e. or >98% e.e., comprising the selective crystallization of the racemic amine of formula (I') in the presence of a chiral, non-racemic acid acid yielding the crystallization of (S)-1-(1-(benzo[d][1,3]dioxol-5-yl)ethyl)piperazine as a salt of formula (Ib'-salt) and leaving in solution the majority of the other enantiomer (R)-1-(1-(benzo[d][1,3]dioxol-5-yl)ethyl)piperazine as a salt of formula (Ia'-salt). After isolation of (S)-1-(1-(benzo[d][1,3]dioxol-5-yl)ethyl)piperazine as a salt, the free base of formula (Ib') can be obtained after a basic treatment and extraction from aqueous phase with suitable solvents, as presented in Scheme 2 and further described below.

Scheme 2

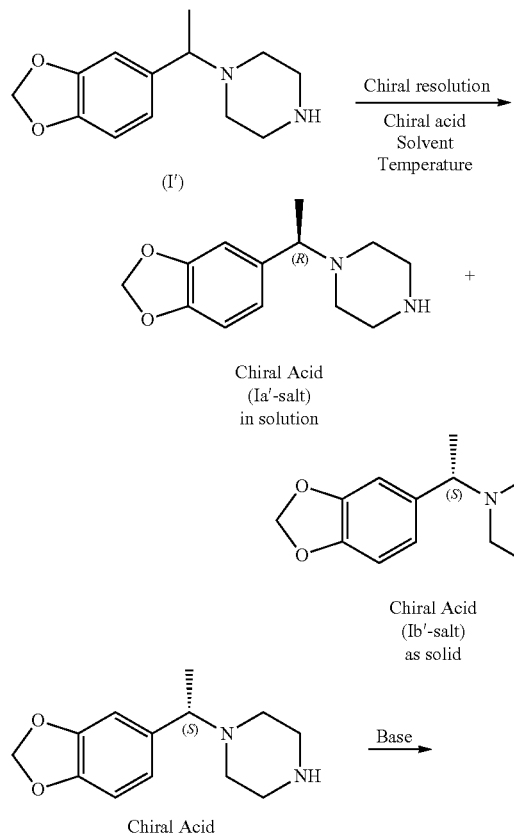

Another preferred racemate or other enantiomeric mixture of a compound of formula I is the compound of formula (I'') (1-(1-(2,3-dihydrobenzofuran-6-yl)ethyl)piperazine), and preferably its racemate:

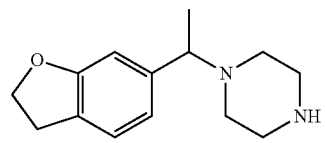

(I'')

In one aspect the present application specifically relates to a process for preparing (S)-1-(1-(2,3-dihydrobenzofuran-6-yl)ethyl)piperazine of formula (Ib'')

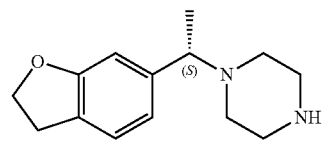

(Ib'')

with high enantiomeric excess (e.e.), preferably with >95% e.e. or >98% e.e., comprising the selective crystallization of the racemic amine of formula (I'') in the presence of a chiral, non-racemic acid acid yielding the crystallization of (S)-1-(1-(2,3-dihydrobenzofuran-6-yl)ethyl)piperazine as a salt of formula (Ib''-salt) and leaving in solution the majority of the other enantiomer (R)-1-(1-(2,3-dihydrobenzofuran-6-yl)ethyl)piperazine as a salt of formula (Ia''-salt). After isolation of (S)-1-(1-(2,3-dihydrobenzofuran-6-yl)ethyl)piperazine as a salt, the free base of formula (Ib'') can be obtained after a basic treatment and extraction from aqueous phase with suitable solvents, as presented in Scheme 3 and further described below.

Scheme 3

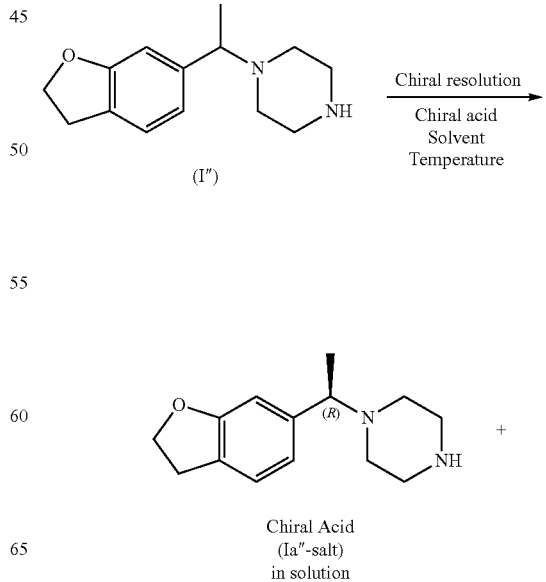

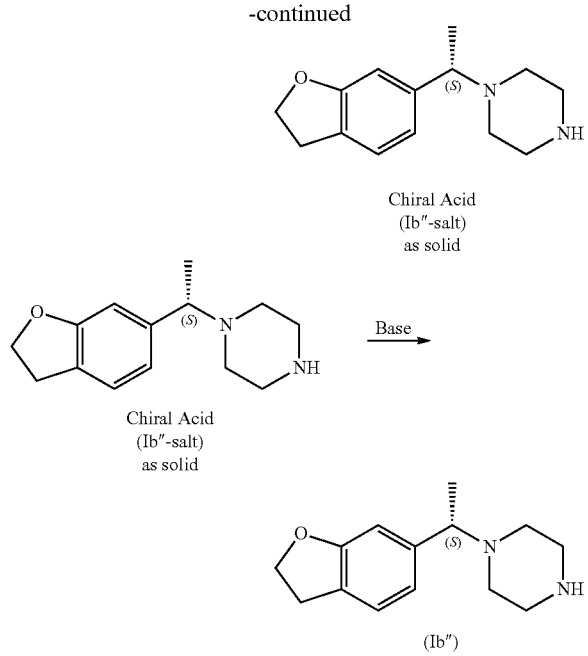

Very preferred chiral acids used for the chiral resolution of compound of formula (I) are selected from (S)-Me-mandelic acid, (S)-4-bromo-mandelic acid, (S)-4-chloro-mandelic acid, (S)-phenylsuccinic acid, Dibenzoyl-D-tartaric acid, D-(+)-Di-tolylyltartaric acid, D-tartaric acid, Di-p-anisoyl-(D)-tartaric acid. These acids are preferably employed, if the S-enatiomer of the respective compound of formula I is desired, as the diastereomeric salts are crystallizing. R-enantiomers of compounds of formula (I) can be either obtained from the respective R-enantiomers of the chiral acids mentioned above or from the liquor after crystallized S-enantiomer of compounds of formula I have been separated therefrom.

Preferably, the chiral acids are used in a molar ratio to the compounds of formula I of between about 1 to 2 (i.e. about 0.5 equivalents based on the compounds of formula I) and about 3 to 1 (i.e. about 3 equivalents), more preferably in a molar ratio of about 1 to 1 (i.e. 1 equivalent) to about 2 to 1 (i.e. about 2 equivalents). Most preferably, about 0.7, about 0.8 or about 0.9 equivalents (based on the compounds of formula I) are used for the selective crystallization according to the invention. Very preferred are about 0.8 equivalents. Solvents and solvent mixtures that are preferably used for the process of the present invention, are $H_2O$, MeCN (Acetonitrile), about 2 to about 50% $H_2O$ in EtOH (Ethanol), EtOH, 2 to 50% $H_2O$ in MeOH (Methanol), MeOH, 2 to 50% $H_2O$ in IPA (Isopropyl Alcohol), IPA, 2 to 50% MeOH in MEK (methyl ethyl ketone, 2-butanone), MEK, 2 to 50% MeOH in iPrOAc (isopropyl acetate), iPrOAc, dioxane. All percentages for solvent mixtures are given in volume percent, if not indicated otherwise.

Preferred conditions for chiral resolutions of compound of formula (I') are listed in Tables 1 and 2 and in the examples below.

TABLE 1

| Entry | Resolving agent (0.9 equiv) | Solvents (volume) | Yield | e.e. solid (Ib') | e.e. filtrate (Ia') |
|---|---|---|---|---|---|
| 1 | (S)-Me-mandelic acid | MEK, 5% $H_2O$ (10 mL) | 28% | 98.3% | 51.2% |
| 2 | (S)-4-bromo-mandelic acid | MeCN, 5% $H_2O$ (20 mL) | N.A. | 93.4% | 17.5% |
| 3 | (S)-4-chloro-mandelic acid | MeCN (20 mL) | N.A. | 77% | 66% |
| 4 | (S)-phenylsuccinic acid | EtOH, 5% $H_2O$ (5 mL) | N.A. | 88.3% | 57.7% |

300 mg of racemic compound of formula (I') has been used for entries 1, 2, 3, 4.

TABLE 2

| Entry | (I') | Resolving agent (equiv) | Solvents (volume) | Yield (Ib') | e.e. solids (Ib') | e.e. filtrate (Ia') |
|---|---|---|---|---|---|---|
| 1 | 10 g | (S)-4-chloro-mandelic acid (0.8 equiv) | $CH_3CN$, 5% $H_2O$ (160 mL) | — | 79% | 15% |
| 2 | Recrystallization of entry 1 | | $CH_3CN$, 5% $H_2O$ (160 mL) | 15% | 99% | |
| 3 | 0.92 g | (S)-phenylsuccinic acid (0.8 equiv) | EtOH, 5% $H_2O$ (7.5 mL) | — | 90% | 62% |
| 4 | Recrystallization of entry 3 | | EtOH, 5% $H_2O$ (7.5 mL) | 34% | 98.4% | 14.1% |

Preferred conditions for chiral resolutions of compound of formula (I") are listed in Tables 3 and 4 and in the examples below.

TABLE 3

| Sr No | Resolving agent | Equi | Solvent | Solvent Volume | ee of Solid | ee of filtrate |
|---|---|---|---|---|---|---|
| 1 | Dibenzoyl-D-tartaric acid | 0.75 | MeOH | 4.5 mL (15 V) | 80.7% | 12.9% |
| 2 | Dibenzoyl-D-tartaric acid | 0.75 | 2%$H_2O$ in MeOH | 3 mL (10 V) | 82.5% | 13.3% |
| 3 | D-(+)-Di-tolylyltartaric acid | 0.5 | MeOH | 4.5 mL (15 V) | 66% | 84% |

TABLE 3-continued

| Sr No | Resolving agent | Equi | Solvent | Solvent Volume | ee of Solid | ee of filtrate |
|---|---|---|---|---|---|---|
| 4 | D-(+)-Di-tolylyltartaric acid | 0.5 | 2%H2O in MeOH | 3 mL (10 V) | 60% | 84% |
| 5 | D-tartaric acid | 0.75 | 2%H2O in MeOH | 3 mL (10 V) | 76% | 75% |
| 6 | Di-p-anisoyl-(D)-tartaric acid | 0.75 | 2%H2O in MeOH | 3 mL (10 V) | 90% | 70% |
| 7 | Di-p-anisoyl-(D)-tartaric acid | 0.75 | MeOH | 4.5 mL (15 V) | 86% | 70% |
| 8 | Di-p-anisoyl-(D)-tartaric acid | 0.5 | 2%H2O in MeOH | 3 mL (10 V) | 92% | 74% |
| 9 | Di-p-anisoyl-(D)-tartaric acid | 0.5 | MeOH | 4.5 mL (15 V) | 84% | 84% |
| 10 | Di-p-anisoyl-(D)-tartaric acid | 0.5 | 5%H2O in MeOH | 3 mL (10 V) | 90% | 70% |
| 11 | Di-p-anisoyl-(D)-tartaric acid | 0.5 | 10%H2O in MeOH | 3 mL (10 V) | 90% | 72% |
| 12 | Di-p-anisoyl-(D)-tartaric acid | 0.5 | 15%H2O in MeOH | 3 mL (10 V) | 92% | 56% |
| 13 | Di-p-anisoyl-(D)-tartaric acid | 0.5 | 10%H2O in MeOH | 3.9 mL (13 V) | 90% | 70% |
| 14 | Di-p-anisoyl-(D)-tartaric acid | 0.5 | 10%H2O in MeOH | 5.1 mL (17 V) | 90% | 70% |
| 15 | Di-p-anisoyl-(D)-tartaric acid | 0.5 | 10%H2O in MeOH | 6 mL (20 V) | 90% | 70% |

For all conditions listed in Table 3, 300 mg of racemic compound of formula (I″) has been used.

TABLE 4

| Entry (I″) | | Resolving agent (equiv) | Solvents (volume) | Yield (Ib″) | e.e. solids (Ib″) | e.e. filtrate (Ia″) |
|---|---|---|---|---|---|---|
| 1 | 8 g | D-Di-p-anisoyltartaric acid (0.5 equiv) | MeOH, 5% H$_2$O (96 mL, 12 V) | — | 91% | 67% |
| 2 | Recrystallization of entry 1 | | MeOH, 5% H$_2$O (80 mL, 10 V) | — | 97% | |
| 4 | Recrystallization of entry 2 | | MeOH, 5% H$_2$O (80 mL, 10 V) | 31% | 98.6% | — |

An enantiomerically enriched mixture denotes a compound of Formula (Ib′), or (Ib″) or related formula having an enantiomeric excess, as measured by methods well known by one skilled in the art, of 10% or more, preferably 50% or more, and more preferably more than 95%. Most preferably an enantiomerically enriched mixture denotes a compound of Formula (Ib′) or (Ib″) or related formulae having an enantiomeric excess of more than 98%.

The present invention also relates to a process for manufacturing compound of formula (Ib′), (Ib″) and to the compound as such.

Moreover, the invention relates to the diastereomeric salts prepared according to the present invention.

Time for crysallisation ranges typically from about 0.5 hours to about 48 hours, such as from about 1 hour to about 24 hours, and at least about 2 hours.

Suitable bases for recovering the basic enantiomer from the respective diasteromeric salt used in the selective crystallisation process of the present invention include sodium hydroxide, potassium hydroxide, sodium carbonate, potassium carbonate lithium hydroxide, and the like, preferably in aqueous solution. Preferably, from about 1.0 to about 4.0 molar equivalents of suitable base with respect to the compounds of formula I are used.

The resolution reactions are preferably heated above room temperature, before allowing to cool to room temperature or to lower temperatures. Preferably, the resolution reactions are preferably heated at the boiling point of the respective solvent or solvent mixture, preferably from about 40° C. to about 120° C. In one embodiment the reaction temperature is about 50° C. to about 100° C. In one embodiment the temperature is raised to at least about 80° C.

The following definitions are used in connection with the present application unless the context indicates otherwise. The term "% e.e." means the enantiomeric excess of a substance, which is defined as the absolute difference between the mole fraction of each enantiomer.

A chiral acid non-racemic acid is used for the resolution of the compounds of formula I. Preferably, these acids are enantiomerically pure or have at least an e.e. of 98% or 99%. These acids include but are not limited to (1R or 1S)-10-camphorsulfonic acid, (1R or 1S)-3-bromocamphor-10-sulfonic acid, (D or L)-tartaric acid and substituted analogues such as (D or L)-diacetyltartaric acid, (D or L)-dibenzoyl tartaric acid, (D or L)-di-O,O'-p-toluoyl-tartaric acid, (D or L)-di-O,O'-o-toluoyl-tartaric acid, (R or S)-1,1″-binaphthyl-2,2″-diyl-hydrogenphosphate, (D or L)-N-acetyl-phenylalanine, (D or L)-acetylmandelic acid, (R or S)-cyclohexylphenylglycolic acid, (S)-camphanic acid, (R or S)-2-pyrrolidone-5-carboxylic acid, naproxen, ibuprofen; (D or L)-malic acid, L-lactic acid, (R or S)-3-hydroxybutyric acid, hyodeoxycholic acid, (R or S)-mandelic acid, (R or S)-Memandelic acid, (R or S)-4-bromo-mandelic acid, (R or S)-4-chloro-mandelic acid or (R or S)-phenylsuccinic acid, or suitable suitable N-protected amino acids (for example (D or L)-N-benzoylproline or (D or L)-N-benzenesulfonylproline), or the various substituted (D or L)-tartaric acids.

Preferred chiral acids are also the following: (−)-Tartaric acid(+)-Camphor sulfonic acid, (2R,3R)-2'-chloro-tartranilic acid (2R,3R)-tartranilic acid, (2S,3S)-2'-methoxy-tartranilic acid, (R)-(−)-2-Chloromandelic acid, (R)-(−)-2-phenylpropionic acid, (R)-4-methyl-mandelic acid, (R)-alpha-methoxy-phenyl acetic acid, (R)-Anisyphos, (R)-BINAP phosphate, (R)-Chlocyphos, (R)-Phencyphos hydrate, (R)-phenylsuccinic acid, (S)-(α-methylbenzyl)phthalamic acid, (S)-'O-acetyl mandelic acid, (S)-4-bromo-mandelic acid, (S)-Mandelic acid, (S)-naproxen, Boc-D-homophenylalanine, Boc-D-phenylalanine, D-(+)-3-Phenyllactic acid, D-Camphoric acid, Dibenzoyl-L-tartaric acid hydrate, D-pyroglutamic acid, L-(−)-Di-p-anisoyltartaric acid, L-(−)-Di-Toluoyltartaric acid, L-Malic acid, L-α-Hydroxyisovaleric acid, N-acetyl-D-Leucine, N-acetyl-L-phenylalanine, N-Acetyl-L-proline.

The following abbreviations refer respectively to the definitions below:

Ac (acetyl), aq (aqueous), h (hour), g (gram), L (liter), mg (milligram), MHz (Megahertz), μM (micromolar), min (minute), mm (millimeter), mmol (millimole), mM (millimolar), m.p. (melting point), equiv (equivalent), mL (milliliter), μL (microliter), ACN (acetonitrile), AcOH (acetic acid), BINAP (2,2'-bis(disphenylphosphino)-1,1'-binaphtalene, BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (Ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)methylene]-dimethyl-ammonium hexafluorophosphate),
HOBt (Hydroxybenzotriazole), HPLC (High Performance Liquid Chromatography), i-PrOH (2-propanol), $K_2CO_3$ (potassium carbonate), LC (Liquid Chromatography), MD Autoprep (Mass directed Autoprep), MeOH (methanol), $MgSO_4$ (magnesium sulfate), MS (mass spectrometry), MTBE (Methyl tert-butyl ether), Mtr. (4-Methoxy-2,3,6-trimethylbenzensulfonyl), MW (microwave), NBS (N-bromo succinimide), $NaHCO_3$ (sodium bicarbonate), $NaBH_4$ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

EXAMPLES

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR or Varian NMR, model Mercury-300. Residual signal of deuterated solvent was used as internal reference. Chemical shifts (δ) are reported in ppm in relative to the residual solvent signal (δ=2.50 for $^1$H NMR in DMSO-$d_6$, and 7.26 in $CDCl_3$). s (singlet), d (doublet), t (triplet), q (quadruplet), br (broad), quint (quintuplet).

The MS data provided in the examples described below were obtained as followed: Mass spectrum: LC/MS Agilent (ESI/APCI), Chemstration, 1200 Series.

LCMS Methods:
Method A
Method: A-0.1% TFA in $H_2O$, B-0.1% TFA in ACN: Flow-2.0 mL/min.
Column: XBridge C8 (50×4.6 mm, 3.5 μm+ve mode
Method B
Method: A-10 mM $NH_4HCO_3$ in $H_2O$, B-ACN: Flow—1.0 mL/min.
Column: XBridge C8 (50×4.6 mm, 3.5 μm), +ve mode
HPLC analyses were obtained using Agilent 1200 Series instruments as followed using % with UV detection (max-plot).
Method A
Method: A-0.1% TFA in $H_2O$, B-0.1% TFA in ACN: Flow—2.0 mL/min.
Column: XBridge C8 (50×4.6 mm, 3.5 μm).
Chiral HPLC Methods:
Chiral HPLC Method A:
Instrument: Waters Acquity UPC2 system with PDA detector and QDA mass detector.
Column: Acquity UPC2 Trefoil CEL2 (3.0×150 mm; 2.5 μm)
Mobile phase A: $CO_2$
Mobile phase B: Ethanol/Acetonitrile/Trifluoroacetic acid 50/50/0.2
Pump Flow: 2.5 ml/min
UV Detection: 240 nm
Injection Volume: 1 μl
Run Time: 6 min
Pump Program: Gradient:

| Time | % A | % B |
|---|---|---|
| 0.0 | 98 | 2 |
| 5.0 | 70 | 30 |
| 5.1 | 98 | 2 |
| 6 | 98 | 2 |

Column Temperature: 40° C.
ABPR: 2500 psi
Mass Detection: MS Scan ES positive and negative
Chiral HPLC Method B:
Instrument: THAR SFC AMDS
Column: Chiralpak ADH (250×4.6) mm, 5 μm)
Mobile phase A: $CO_2$
Mobile phase B: 20 mM Ammonia in Methanol
Pump Flow: 2.1 ml/min
UV Detection: 220 nm
Injection Volume: 5 μl
Run Time: 10 min
Column Temperature: 35° C.
Pump Program: Gradient:

| Time | % A | % B |
|---|---|---|
| 0.0 | 70 | 30 |
| 10 | 70 | 30 |

The chiral HPLC methods described below may preferably be performed on an Agilent 1260 DAD instrument.

Chiral HPLC: (Method D)
Mobile Phase: 0.1% DEA in Hexane:EtOH: 80:20; FLOW: 1.0 mL\min;
COLUMN: Chiralcell OJ-H column (250×4.6) mm, 5 μm Chiral HPLC: (Method F)
Mobile Phase: 0.1% DEA in Hexane:EtOH: 70:30; FLOW: 1.0 mL\min;
COLUMN: Chiralpak IA (250×4.6) mm, 5 μm Chiral HPLC: (Method G)
Mobile Phase: 0.1% DEA in Hexane:EtOH: 60:40; FLOW: 1.0 mL\min;
COLUMN: Chiralcel OD-H (250×4.6) mm, 5 μm MD Autoprep Conditions
The mass directed preparative HPLC purifications were performed with a mass directed autopurification Fractionlynx from Waters.

Method A
0.1% HCOOH in $H_2O$, B-MeOH or ACN, Column: Symmetry C8 (300 mm×19 mm), 7 μm Method B
0.1% TFA in $H_2O$, B-MeOH or ACN, Column: Symmetry C8 (300 mm×19 mm), 7 μm Method C
10 mM $NH_4HCO_3$ in $H_2O$, B-MeOH or ACN, Column: Symmetry C8 (300 mm×19 mm), 7 μm Method D
10 mM $NH_4OAC$ in $H_2O$, B-MeOH or ACN, Column: Symmetry C8 (300 mm×19 mm), 7 μm Preparative HPLC Conditions
Chiral Preparative Method PD:
Mobile phase: n-Hexane, IPA; Column: Chiral pak AD-H (20×250) mm, 5 micron, Flow: 12 mL/min Chiral Preparative Method PF:
Mobile Phase: 0.1% DEA in Hexane:EtOH: 80:20; FLOW: 12.0 mL\min;
COLUMN: Chiralcell OJ-H column (250×20) mm, 5 μm The SFC purifications were performed with a Prep SFC, THAR-SFC 80 and THAR-SFC 200.

SFC Preparative Chiral Method PA:
COLUMN: YMC Cellulose SB (250×30) mm, 5 μm; CO-SOLVENTS: 0.5%
DEA in Methanol 40%; FLOW: 60 mL/min;

General Procedure for Chlorination of Hetrocyclic Alcohol: Procedure A

To a stirred solution of alcohol (1 equiv) in dry DCM (10 to 20 mL), thionyl chloride (1.7 to 3 equiv) was added slowly at 0° C. The reaction mixture was warmed to rt and was refluxed for 1 h. The reaction mixture was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum to give chloro compound.

General Procedure for N-Alkylation: Procedure B

To a stirred solution of amine (1 mmol/0.8 to 1 equiv) in dry DMF (5 to 10 mL), chloro compound (1.0 to 1.2 equiv) and potassium carbonate (2 equiv) were added at rt. The resulting mixture was heated at 90° C. for 16 h. It was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum. The crude products were purified by flash chromatography to afford the desired product.

Example 1: 6-(1-chloroethyl)-2,3-dihydrobenzo[b][1,4]dioxine

Step 1: 1-(2,3-dihydrobenzo[b][1,4]dioxin-6-yl)ethan-1-ol

The title compound was synthesized with same protocol as described for Example 4, Step 1, using 1-(2,3-dihydrobenzo[b][1,4]dioxin-6-yl)ethan-1-one (2.0 g, 11.2 mmol) and $NaBH_4$ (0.49 g, 13 mmol). The resulting crude alcohol was used as such in the next step. Yield: 99% (2.0 g, colorless liquid). $^1$H NMR (400 MHz, DMSO-$d_6$): δ 6.80 (s, 1H), 6.79-6.76; (m, 2H), 4.59; (q, J=5.6 Hz, 1H), 4.20; (s, 4H), 1.26; (d, J=5.6 Hz, 3H). LCMS: (Method B) 163.0 (Hydroxy elimination mass), Rt. 2.51 min, 99.4% (Max).

Step 2: 6-(1-chloroethyl)-2,3-dihydrobenzo[b][1,4]dioxine

The title compound was synthesized according to the general procedure A. It was used in the next step without further purification. Yield: 90% (2.2 g, brown liquid). $^1$H NMR (400 MHz, DMSO-$d_6$): δ 6.97 (s, 1H), 6.96-6.92; (m, 1H), 6.84-6.82; (m, 1H), 5.26; (t, J=6.7 Hz, 1H), 4.23; (s, 4H), 1.75; (d, J=6.7 Hz, 3H). LCMS: (Method A) 163.0; (Cl-Elimination mass), Rt. 3.66 min, 95.3% (Max).

Example 2: Hydrochloride salt of 1-(1-(2,3-dihydrobenzo[b][1,4]dioxin-6-yl)ethyl)piperazine Step 1: t-Butyl 4-(1-(2,3-dihydrobenzo[b][1,4]dioxin-6-yl)ethyl)piperazine-1-carboxylate The title compound was synthesized according to the general procedure B, starting with 6-(1-chloroethyl)-2,3-dihydrobenzo[b][1,4]dioxine of example 1 (5 g, 25.2 mmol) and N-boc piperazine (3.96 g, 21.2 mmol). The crude product was purified by flash chromatography, affording the title compound. Yield: 52% (4.6 g, brown liquid). $^1$H NMR (400 MHz, DMSO-$d_6$): δ 6.80-6.71; (m, 3H), 4.21; (s, 5H), 3.34-3.26; (m, 4H), 2.27-2.24; (m, 4H), 1.37; (s, 9H), 1.23; (d, J=6.7 Hz, 3H). LCMS: (Method A) 349.2; (M+H), Rt. 3.19 min, 80.9% (Max).

The S-enantiomer of this compound can be obtained from the racemate by applying the processes and conditions described in examples 10, 11, 12, 13, 14 and 15.

Step 2: Hydrochloride Salt of 1-(1-(2,3-dihydrobenzo[b][1,4]dioxin-6-yl)ethyl)piperazine To a stirred solution of tert-butyl 4-(1-(2,3-dihydrobenzo[b][1,4]dioxin-6-yl)ethyl)piperazine-1-carboxylate (4.6 g, 13.20 mmol) in dry dioxane (5.0 mL), HCl in dioxane (10.0 mL, 4 M, Spectrochem) was added at 0° C. The reaction mixture was stirred at rt for 2 h. The completion of the reaction was monitored by TLC. The reaction mixture was concentrated. Diethyl ether was added and was evaporated again, affording the title compound. Yield: 89% (3.8 g, off white solid). $^1$H NMR (400 MHz, DMSO-$d_6$): δ 12.08 (br. s, 1H), 9.48-9.18; (m, 2H), 7.18; (s, 1H), 7.03; (s, 1H), 6.92; (d, J=10.6 Hz, 1H), 4.49; (s, 1H), 4.24; (s, 4H), 3.41-3.15; (m, 4H), 2.91-2.71; (m, 4H), 1.64; (s, 3H). LCMS: (Method A) 249.2; (M+H), Rt. 1.64 min, 92.6% (Max).

Example 3: 1-(1-(2,3-dihydrobenzo[b][1,4]dioxin-6-yl)ethyl)piperazine 20 g of the hydrochloride salt of 1-(1-(2,3-dihydrobenzo[b][1,4]dioxin-6-yl)ethyl)piperazine were suspended in NaOH solution (1 M, 150 mL) and extracted with EtOAc (150 mL). The water layer was further extracted two times with EtOAc (50 mL). The combined organic layers were dried over MgSO$_4$ and filtered off. After evaporation of the solvent, the title compound was isolated as an oil.

Example 4: 5-(1-chloroethyl)benzo[d][1,3]dioxide

Step 1: 1-(Benzo[d][1,3]dioxo-5-yl)ethan-1-ol

To a stirred solution of 3,4-methylenedioxy acetophenone (4.5 g, 27 mmol, Alfa aesar) in dry MeOH (50 mL), NaBH$_4$ (1.08 g, 42 mmol, Loba chemie) was added slowly at 0° C. The reaction mixture was stirred at room temperature for 1 h. Then the reaction mixture was concentrated under vacuum and diluted with DCM. The DCM layer was washed with water, brine and dried over anhydrous Na$_2$SO$_4$. The solvent was removed under reduced pressure and resulting crude alcohol was used as such in the next step. Yield: 90% (4.0 g, colorless liquid). $^1$H NMR (400 MHz, CDCl$_3$): δ 6.89; (s, 1H), 6.89-6.75; (m, 2H), 5.95; (s, 2H), 4.81; (t, J=8.0 Hz, 1H), 1.46; (d, J=8.0 Hz, 3H). LCMS: (Method B) 149.0; (Hydroxy elimination mass), Rt. 2.51 min, 98.6% (Max).
HPLC: (Method A) Rt. 2.499 min, 99.5% (Max).

Step 2: 5-(1-Chloroethyl)benzo[d][1,3]dioxole

The title compound was synthesized by following general procedure A. It was used for next step without further purification. Yield: 72% (1.2 g, colorless liquid). $^1$H NMR (400 MHz, DMSO-d$_6$): δ 7.06; (d, J=4.0 Hz, 1H), 6.93; (d, J=8.0 Hz, 1H), 6.86; (d, J=8.0 Hz, 1H), 6.01; (s, 2H), 2.49; (q, J=8.0 Hz, 1H), 1.74; (d, J=8.0 Hz, 3H). LCMS: (Method B) 149.0 (Cl-Elimination mass), Rt. 3.71 min, 80.15% (Max).

Example 5: Hydrochloride salt of 1-(1-(benzo[d][1,3]dioxol-5-yl)ethyl)piperazine

Step 1: tert-butyl 4-(1-(benzo[d][1,3]dioxol-5-yl)ethyl)piperazine-1-carboxylate The title compound was synthesized following general procedure B, starting with 5-(1-Chloroethyl)benzo[d][1,3]dioxole of example 4 and N-boc piperazine. The crude product was purified by flash chromatography, affording the title compound (yellow solid). $^1$H NMR (400 MHz, DMSO-d$_6$): δ 6.85-6.82; (m, 2H), 6.74-6.71; (m, 1H), 5.98; (m, 2H), 3.37-3.36; (m, 1H), 3.27; (br. s, 4H), 2.28-2.21; (m, 4H), 1.37; (s, 9H), 1.25; (d, 3H, J=6.8 Hz). LCMS: (Method A) 335.2; (M+H), Rt. 3.10 min, 93.15% (Max). HPLC: (Method A) Rt. 3.12 min, 95.01% (Max).

Step 2: Hydrochloride Salt of 1-(1-(Benzo[d][1,3]dioxol-5-yl)ethyl)piperazine To a stirred solution of tert-butyl 4-(1-(benzo[d][1,3]dioxol-5-yl)ethyl)piperazine-1-carboxylate (1.8 g, 5.38 mmol) in dry dioxane (10 mL), HCl in dioxane (10 mL, 4 M, Spectrochem) was added at rt and stirred for 2 h at same temperature. The reaction mixture was concentrated under vacuum and the resulting crude product was washed with diethyl ether to afford the title product as hydrochloride salt. Yield: 82% (1.2 g, off white solid). $^1$H NMR (400 MHz, DMSO-d$_6$): δ 12.29; (s, 1H), 7.34; (s, 1H), 7.08; (d, 1H, J=7.7 Hz), 7.00; (d, 1H, J=7.9 Hz), 6.07; (s, 2H), 4.54; (br. s, 1H), 3.81; (br. s, 1H), 3.49-3.42; (m, 3H), 3.33; (br. s, 2H), 3.12; (br. s, 1H), 2.99; (br. s, 1H), 1.67; (d, 3H, J=5.7 Hz). LCMS: (Method A) 235.0; (M+H), Rt. 1.65 min, 98.08% (Max). HPLC: (Method A) Rt. 1.56 min, 99.86% (Max).

Example 6: 1-(1-(benzo[d][1,3]dioxol-5-yl)ethyl)piperazine

The hydrochloride salt of 1-(1-(benzo[d][1,3]dioxol-5-yl)ethyl)piperazine (20 g) was suspended in NaOH solution (1 M, 150 mL) and extracted with EtOAc (150 mL). The water layer was further extracted two times with EtOAc (50 mL). The combined organic layers were dried over MgSO$_4$ and filtered off. After evaporation of the solvent, the title compound was isolated as an oil (10 g). The aqueous layer was further basified to pH 12 (pH after the extraction was around 7-8) by addition of 2 M NaOH solution and further extracted with EtOAc. A second batch of the title compound (5 g) was isolated.

Example 7: 6-(1-chloroethyl)-2,3-dihydrobenzofuran

Method 1

Step 1: 1-(2,3-dihydrobenzofuran-6-yl)ethan-1-one

The title compound was prepared according to procedures reported in the literature and known by persons skill in the art, using 6-bromo-2,3-dihydro-1-benzofuran (1 g, 5.03 mmol) as starting material. In a preferred method, 6-bromo-2,3-dihydro-1-benzofuran (1 g, 5.03 mmol) in toluene (10 mL) was degassed for 30 min. To this solution, 1-ethoxy vinyl tributyltin (2.012 g, 5.53 mmol) and bis(triphenylphosphine)palladium dichloride (0.35 g, 0.50 mmol) were added at rt and stirred for 16 hours at 90° C. The reaction mixture was cooled to rt and filtered through celite. After evaporation of the solvent, 6 N HCl solution in water (10 mL) was added and the mixture was stirred for 1 hour at rt. It was concentrated and neutralized with sat. NaHCO$_3$. The desired product was extracted with DCM (50 mL), dried over Na$_2$SO$_4$ and concentrated. The crude product was purified by flash chromatography to give the title compound. Yield: 73.7% (0.6 g, pale yellow solid). $^1$H NMR (400 MHz, DMSO-d$_6$): δ 7.48; (d, J=7.64 Hz, 1H), 7.37-7.35; (d, J=7.68 Hz, 1H), 7.26; (s, 1H), 4.58; (t, J=8.76 Hz, 2H), 3.24; (t, J=8.76 Hz, 2H), 2.53; (s, 3H). LCMS: (Method A) 163.2 (M+H), Rt. 3.01 min, 97.60% (Max).

Step 2: 1-(2,3-dihydrobenzofuran-6-yl)ethan-1-ol

The title compound was prepared according to procedures reported in the literature and known by persons skill in the art, using 1-(2,3-dihydrobenzofuran-6-yl)ethan-1-one (0.6 g, 3.7 mmol) as starting material. In a preferred method, to a stirred solution of 1-(2,3-dihydrobenzofuran-6-yl)ethan-1-one (0.6 g, 3.7 mmol) in methanol (10 mL), sodium borohydride (281 mg, 7.4 mmol) was added slowly at 0° C. and stirred 1.5 h. The completion of the reaction was monitored by TLC and the solvents were evaporated at 45° C. under vacuum. The residue was diluted with EtOAc (25 mL) and washed with water (25 mL), brine solution (25 mL) and dried over Na$_2$SO$_4$. After evaporation of the solvent, the title compound was isolated and used without further purification. Yield: 88.30% (0.53 g, colourless liquid). $^1$H NMR (400 MHz, DMSO-d$_6$): δ 7.11; (d, J=7.6 Hz, 1H), 6.77-6.75; (m, 1H), 6.71; (s, 1H), 5.04; (d, J=4.4 Hz, 1H), 4.63-4.61; (m, 1H), 4.48; (t, J=8.8 Hz, 2H), 3.11; (t, J=8.8 Hz, 2H), 1.25; (d, J=6.4 Hz, 3H). LCMS: (Method A) 147.0 (M-17H), Rt. 2.64 min, 89.95% (Max).

Step 3: 6-(1-chloroethyl)-2,3-dihydrobenzofuran

The title compound was synthesized from 1-(2,3-dihydrobenzofuran-6-yl)ethan-1-ol (0.53 g, 3.23 mmol), according to the general procedure B. The crude product was used in the next step without further purification. Yield: quatitative (0.58 g, brown oil). $^1$H NMR (400 MHz, DMSO-d$_6$): δ 7.20 (d, J=7.56 Hz, 1H), 6.93-6.91; (m, 1H), 6.87; (s, 1H), 5.29-5.24; (m, 1H), 4.53; (t, J=8.72 Hz, 2H), 3.15; (t, J=8.76 Hz, 2H), 1.75; (d, J=6.76 Hz, 3H). LCMS: (Method A) 147.0 (M-35H), Rt. 3.76 min, 83.62% (Max).

Method 2

Step 1: 2-(2,5-dibromophenoxy)ethan-1-ol

To a stirred solution of 1,4-dibromo-2-fluorobenzene (Combi-Blocks, 1000 g, 3938 mmol) in ethylene glycol (5100 mL), NMP (500 mL) was added at rt under nitrogen atmosphere. Then potassium tert-butoxide (1547 g, 1378 mmol) was added in portion over 45 min at 5° C. and the resulting mixture was heated to 90° C. for 16 h. Completion of the reaction was monitored by HPLC. The reaction mixture was cooled to rt and diluted with water (2000 mL) and stirred for 15 min at rt. The resultant solid was filtered and washed with ethylene glycol (300 mL×2). To the filtrate, water (16000 mL) was added. The mixture was cooled to 10° C. and stirred 1 h at the same temperature to get solid. The solid was filtered and washed with water (1000 mL×2), pet ether (3×1000 mL) and dried. This solid was mixed with toluene and toluene was evaporated. This process was repeated 3 times (3×500 mL) to give the title compound. Yield: 78% (910 g, White solid). $^1$H NMR (400 MHz, CDCl$_3$): δδ 7.41; (d, J=8.0 Hz, 1H), 7.06-7.00; (m, 2H), 4.14; (t, J=4.0 Hz, 2H), 4.01; (q, J=3.6 Hz, 2H). LCMS: (Method A) 296.0; (M+H), Rt. 3.97 min, 98.16% (Max). HPLC: (Method A) Rt. 3.67 min, 99.53% (Max), 99.38% (220 nm).

Step 2: 1,4-dibromo-2-(2-bromoethoxy)benzene

To a stirred solution of 2-(2,5-dibromophenoxy)ethan-1-ol (910.0 g, 3074.0 mmol) in Toluene (6370 mL), PBr$_3$ (Aldrich, 145 mL, 1541 mmol,) was added under nitrogen atmosphere at 0° C. over 15 min and the resulting mixture was heated to 90° C. for 4 h. It was then cooled to 0° C. and PBr$_3$ (13.57 mL, 142.92 mmol) was added slowly. Then water (20 mL) was added slowly over 20 min. The resulting mixture was heated for 3 h at 90° C. Completion of the reaction was monitored by TLC. The reaction mixture was cooled to 10° C. and quenched with 1N NaOH solution (2200 mL). A milky solid was formed and was filtered off through celite pad. The organic layer was separated and washed with water (1820 mL), brine solution (1820 mL), dried over sodium sulphate and evaporated at 45° C. under vacuum. The resulting crude product was dissolved in ethyl acetate (3185 mL), washed with water (1820 mL), brine solution (1820 mL), dried over sodium sulphate and evaporated at 40° C. under reduced pressure to give the title compound. Yield: 86% (946 g, white solid). $^1$H NMR (400 MHz, DMSO-d$_6$): δ 7.54; (d, J=8.4 Hz, 1H), 7.36; (d, J=1.6 Hz, 1H), 7.13-7.10; (m, 1H), 4.45; (t, J=1.2 Hz, 2H), 3.82; (t, J=1.6 Hz, 2H). HPLC: (Method A) Rt. 4.72 min, 93.03% (Max), 92.82% (220 nm).

Step 3: 2,3-dihydrobenzofuran-6-carbaldehyde

To a stirred solution of 1,4-dibromo-2-(2-bromoethoxy)benzene (946 g, 2635.0 mmol) in dry THF (9.5 L) under nitrogen atmosphere, n-butyl lithium (1812 mL, 2899.0 mmol, 1.6 M in hexane) was added slowly over 30 min at −78° C. After 1 h at the same temperature second lot of n-butyl lithium (1812 mL, 2899.0 mmol, 1.6 M in hexane) was added slowly over 30 min at −78° C. and the resulting mixture was stirred for an additional hour. DMF (408 mL, 5271 mmol) was added slowly at the same temperature and the mixture was stirred for 45 min. The reaction mass was warmed up to 10° C. and it was quenched with the slow additiona of sat. NH$_4$Cl solution (3784 mL). The reaction mixture was extracted with ethyl acetate (2838 mL×2). The combined organic layer was washed with water (2838 mL), brine solution (2838 mL), dried over sodium sulphate and evaporated at 40° C. under reduced pressure to give the title compound. Yield: 96% crude (404 g, brown gum). $^1$H NMR (400 MHz, DMSO-d$_6$): δ 9.90; (s, 1H), 7.45; (t, J=5.2 Hz, 2H), 7.19; (s, 1H), 4.60; (t, J=8.7 Hz, 2H), 3.27; (t, J=8.7 Hz, 2H). HPLC: (Method A) Rt. 2.88 min, 84.34% (Max), 79.35% (220 nm).

Step 4: 1-(2,3-dihydrobenzofuran-6-yl)ethan-1-ol

To a stirred solution of 2,3-dihydrobenzofuran-6-carbaldehyde (404 g, 2726.0 mmol) in dry THF (4040 mL) under nitrogen atmosphere, methyl magnesium chloride solution (1819 mL, 5452.0 mmol, 3 M in THF) was added slowly over 30 min at 0° C. The resulting mixture was stirred for 2 h at rt. Completion of the reaction was monitored by TLC. Reaction mixture was quenched with the addition of sat.NH$_4$Cl solution (1616 mL) and was extracted with ethyl acetate (2×2828 mL). The combined organic layer was washed with water (1616 mL), brine solution (1616 mL), dried over sodium sulphate and evaporated at 45° C. under reduced pressure. The resulting crude product was purified by flash chromatography (Silica gel: 60-120, Eluent: 18% ethyl acetate in pet ether) to give the title compound. Yield: 46% (210 g, brown gum). $^1$H NMR (400 MHz, DMSO-d$_6$): δ 7.12; (d, J=7.2 Hz, 1H), 6.77; (dd, J=0.8, 7.6 Hz, 1H), 6.72; (s, 1H), 5.05; (d, J=4.4 Hz, 1H), 4.66-4.60; (m, 1H), 4.48; (t, J=8.4 Hz, 2H), 3.12; (t, J=8.4 Hz, 2H), 1.28; (t, J=6.8 Hz, 3H). LCMS: (Method A) 147.0 (M+H) (alkene), Rt. 2.65 min, 90.72% (Max). HPLC: (Method A) Rt. 2.62 min, 91.67% (Max), 91.31% (220 nm).

Step 5: 6-(1-chloroethyl)-2,3-dihydrobenzofuran

To a stirred solution of 1-(2,3-dihydrobenzofuran-6-yl) ethan-1-ol (200 g, 1.2195 mmol) in DCM (1600 mL) cooled to 0° C. were added oxalyl chloride (155 mL, 3.6585 mmol) and a catalytic amount of DMF (2 mL) and the mixture was stirred at rt for 16 h. It was concentrated under vacuum and co-distilled with dry DCM (3×500 mL) to afford the titled compound. Yield: 97% (crude) (220 g, brown gummy). $^1$H NMR (400 MHz, DMSO-d$_6$): δ 7.32; (d, J=7.6 Hz, 1H), 6.92; (d, J=9.6 Hz, 2H), 5.28; (q, J=13.2 Hz, 1H), 4.52; (t, J=8.4 Hz, 2H), 3.15; (t, J=8.8 Hz, 2H), 1.75; (d, J=8.4 Hz, 3H). LCMS: (Method A) 147.2 (M+H-Chloro), Rt. 4.19 min, 77.18% (Max).

Example 8: 1-(1-(2,3-dihydrobenzofuran-6-yl)ethyl) piperazine, hydrochloride Step 1: tert-butyl 4-(1-(2, 3-dihydrobenzofuran-6-yl)ethyl)piperazine-1-carboxylate To a stirred solution of N-boc piperazine (5.5 g, 29.5 mmol), TEA (11.9 g, 11.8 mmol) in DMF (55 mL), Example 7 (7.5 g, 41.3 mmol) was added at RT and the resulting mixture was heated at 70° C. overnight. Completion of the reaction was monitored by TLC. The reaction mixture was concentrated under reduced pressure and the resulting crude mixture was dissolved in EtOAc (100 mL). The organic layer was washed with water (50 mL), brine (50 mL), dried over $Na_2SO_4$ and concentrated. The crude product was purified by flash chromatography (12% EtOAc in pet ether as eluent) to give the title compound. Yield: 52% (58% purity) (5.1 g, brown gum). $^1$H NMR (400 MHz, $CDCl_3$): δ 7.19-7.12; (m, 1H), 6.88-6.77; (m, 2H), 4.62-4.59; (m, 2H), 3.42-3.39; (m, 4H), 3.36-3.31; (m, 1H), 3.23-3.18; (m, 2H), 2.44-2.34; (m, 4H), 1.46; (s, 9H), 1.35 (d, J=6.4 Hz, 3H). LCMS: (Method A) 333.3; (M+H), Rt. 3.12 min, 58.09% (Max).

The S-enantiomer of this compound can be obtained from the racemate by applying the processes and conditions described in examples 10, 11, 12, 13, 14 and 15.

Step 2:
1-(1-(2,3-dihydrobenzofuran-6-yl)ethyl)piperazine, hydrochloride

To a stirred solution of tert-butyl 4-(1-(2,3-dihydrobenzofuran-6-yl)ethyl)piperazine-1-carboxylate (5.1 g, 15.3 mmol) in 1,4 dioxane (25 mL), HCl solution in dioxane (4 M, 25 mL) was added at 0° C. The resulting mixture was stirred at rt for 2 h. Completion of the reaction was monitored by TLC. The reaction mixture was evaporated at 40° C. under reduced pressure. The resulting product was triturated with n-hexanes (2×100 mL) and decanted two times. It was then dried at 40° C. under reduced pressure to give the title compound. Yield: 66.2% (3.1 g, Off white solid). $^1$H NMR (400 MHz, DMSO-d6): δ 7.15; (d, J=7.2 Hz, 1H), 6.76-6.71; (m, 2H), 4.36-4.30; (m, 2H), 3.55-3.53; (m, 4H), 3.43-3.41; (m, 1H), 3.15-3.11; (m, 2H), 2.53-2.43; (m, 4H), 1.31-1.29; (m, 3H). LCMS: (Method A) 233.2; (M+H), Rt. 1.67 min, 90.31% (Max).

Example 9:
1-(1-(2,3-dihydrobenzofuran-6-yl)ethyl)piperazine

Method 1

20 g of the hydrochloride salt of 1-(1-(2,3-dihydrobenzofuran-6-yl)ethyl)piperazine, hydrochloride were suspended in NaOH solution (1 M, 150 mL) and extracted with EtOAc (150 mL). The water layer was further extracted two times with EtOAc (50 mL). The combined organic layers were dried over $MgSO_4$ and filtered off. After evaporation of the solvent, the title compound was isolated as an oil.

The S-enantiomer of this compound can be obtained from the racemate by applying the processes and conditions described in examples 10, 11, 12, 13, 14 and 15.

Method 2

Step 1: tert-butyl 4-(1-(2,3-dihydrobenzofuran-6-yl) ethyl)piperazine-1-carboxylate To a stirred solution of tert-butyl piperazine-1-carboxylate (562 g, 30219 mmol) in DMF (2000 mL) was added Example 7 (220 g, 120879 mmol) in DMF (400 mL) and the mixture was stirred at 50° C. for 20 h. The reaction mixture was diluted with water (500 mL) and extracted with EtOAc (2×1000 mL). The organic layer was washed with brine (500 mL) and dried over $Na_2SO_4$. The resulting crude product was purified by flash chromatography (eluent: 22% EtOAc in pet ether), affording the titled compound. Yield: 35% (210 g, Yellow gummy solid). $^1$H NMR (400 MHz, DMSO-$d_6$): δ 7.13; (d, J=8.0 Hz, 1H), 6.73-6.67; (m, 2H), 4.49; (t, J=8.8 Hz, 2H), 3.33-3.26; (m, 5H), 3.14-3.06; (m, 2H), 2.33-2.22; (m, 4H), 1.45; (s, 9H), 1.25; (d, J=6.4 Hz, 3H). LCMS: (Method A) 333.0 (M+H), Rt. 3.17 min, 71.80% (Max).

The S-enantiomer of this compound can be obtained from the racemate by applying the processes and conditions described in examples 10, 11, 12, 13, 14 and 15.

Step 2:
1-(1-(2,3-dihydrobenzofuran-6-yl)ethyl)piperazine

To a stirred solution of tert-butyl 4-(1-(2,3-dihydrobenzofuran-6-yl)ethyl)piperazine-1-carboxylate (202 g, 608.4 mmol) in 1,4 dioxane (300 mL), HCl in dioxane (4M, 1000 mL) was added at 0° C. The resulting mixture was stirred at rt for for 19 h. The reaction completion was monitored by HPLC. The resulting precipitate was then filtered and washed with 1,4 dioxane (200 ml), EtOAc (200 mL), acetonitrile (200 mL) and diethyl ether (200 mL). The solid was dissolved in water (350 mL) and extracted with EtOAc (300 mL×3). Then the aqueous layer was basified with 5N NaOH solution (300 mL) until the pH=13 and was extracted with EtOAc (300 mL×2). The combined organic layer was dried over $Na_2SO_4$ and concentrated to give the crude product. It was purified by column chromatography on silica gel (60-120 mesh) using 10% MeOH in DCM to give the title compound. Yield: 73% (103 g, off white solid). $^1$H NMR (400 MHz, DMSO-$d_6$): δ 7.12; (d, J=7.2 Hz, 1H), 6.72-6.66; (m, 2H), 4.52-4.46; (m, 2H), 3.19-3.01; (m, 5H), 2.64-2.61; (m, 4H), 2.26-2.11; (m, 4H), 1.21; (d, J=6.4 Hz, 3H). LCMS: (Method A) 233.0 (M+H), Rt. 1.66 min, 92.06% (Max).

The S-enantiomer of this compound can be obtained from the racemate by applying the processes and conditions described in examples 10, 11, 12, 13, 14 and 15.

Example 10: Resolution of 1-(1-(benzo[d][1,3]dioxol-5-yl)ethyl)piperazine with (S)-phenylsuccinic Acid: Preparation of (S)-1-(1-(benzo[d][1,3]dioxol-5-yl)ethyl)piperazine (S)-phenylsuccicinic Acid 1-(1-(benzo[d][1,3]dioxol-5-yl)ethyl)piperazine of Example 6 (5.0 g, 21.34 mmol, 1.0 eq) was mixed with (S)-phenylsuccinic acid (3.3 g, 17.04 mmol, 0.8 eq) in ethanol containing 5% of water (40 mL) and the mixture was heated until complete dissolution. The mixture was allowed to cool to room temperature and stirred overnight before the solid was collected by filtration and washed with ethanol. The optical purities of the solid and filtrate were 87% e.e. and 70% e.e. respectively. The solid was dissolved in refluxing ethanol containing 5% of water (40 mL). The mixture was allowed to cool to room temperature and stirred overnight before the solid was collected by filtration and washed with ethanol. The optical purity of the solid was 98% e.e. The latter was dried in vacuo to furnish the title product (2.79 g, 30% yield). ¹H NMR shows a 1:1 ratio with the salt.

Mp=170.4–172.2° C.

¹H NMR (300 MHz, CD₃OD): δ 7.42-7.12; (m, 5H), 8.85; (s, 1H), 6.75; (s, 2H), 5.91; (s, 2H), 4.02-3.83; (m, 1H), 3.52-3.37; (m, 1H), 3.36-3.25; (m, 2H), 3.07-2.92; (m, 2H), 2.77-2.43; (m, 6H), 1.35; (d, J=5.7 Hz, 3H).

Chiral HPLC Method A: e.e.=98.08% (enantiomeric purity=99.04%)

Example 11: (S)-1-(1-(benzo[d][1,3]dioxol-5-yl)ethyl)piperazine

The solid salt obtained in Example 10 is treated according to example 6, in order to obtain the free base (S)-1-(1-(benzo[d][1,3]dioxol-5-yl)ethyl)piperazine (light yellow oil).

Chiral HPLC Method A: e.e.=97.64% (enantiomeric purity=98.82%)

Example 12: Resolution of 1-(1-(benzo[d][1,3]dioxol-5-yl)ethyl)piperazine with (S)-4-chloromandelic Acid: Preparation of (S)-1-(1-(benzo[d][1,3]dioxol-5-yl)ethyl)piperazine (S)-4-chloromandelic Acid 1-(1-(benzo[d][1,3]dioxol-5-yl)ethyl)piperazine of Example 6 (9.63 g, 41.10 mmol, 1.0 eq) was mixed with (S)-4-chloromandelic acid (6.2 g, 32.88 mmol, 0.8 eq) in acetonitrile (160 ml) containing 5% of water and the mixture was heated until complete dissolution. The mixture was allowed to cool to room temperature and stirred overnight before the solid was collected by filtration and washed with acetonitrile. The optical purities of the solid and filtrate were 80% e.e. and 15% e.e. respectively. The solid was dissolved in refluxing acetonitrile containing 5% of water. The mixture was allowed to cool to room temperature and stirred overnight before the solid was collected by filtration and washed with acetonitrile. The optical purity of the solid was 99% e.e. The latter was dried in vacuo to furnish the title product (2.66 g, 15% yield). ¹H NMR shows a 1:1 ratio with the salt.

Mp=164.8-166.8° C.

¹H NMR (300 MHz, CDCl₃): δ 7.48-7.35; (m, 2H), 7.34-7.27; (m, 2H), 6.84-6.59; (m, 3H), 5.95; (s, 2H), 4.82; (s, 1H), 3.25-3.11; (m, 1H), 2.94-2.69; (m, 4H), 2.56-2.19; (m, 4H), 1.33-1.21; (m, 3H).

Chiral HPLC Method A: e.e.=98.78% (enantiomeric purity=99.39%)

Example 13: (S)-1-(1-(benzo[d][1,3]dioxol-5-yl)ethyl)piperazine

The solid salt obtained in Example 12 is treated according to Example 6, in order to obtain the free base (S)-1-(1-(benzo[d][1,3]dioxol-5-yl)ethyl)piperazine.

Example 14: Resolution of 1-(1-(2,3-dihydrobenzofuran-6-yl)ethyl)piperazine with D-Di-p-anisoyltartaric Acid: Preparation of (S)-1-(1-(2,3-dihydrobenzofuran-6-yl)ethyl)piperazine D-Di-p-anisoyltartaric Acid To a stirred solution of Example 9 (102 g, 439.7 mmol) in 5% water in MeOH (1236 mL, 12V), D-di-p-anisoyltartaric acid (92.86 g, 219.8 mmol) was added at rt. The mixture was refluxed for 30 min. All the material was initially dissolved. When the salt was formed it precipitated as a white solid. The mixture was stirred overnight at room temperature and the solid was collected by filtration and washed twice with 5% of water in methanol (2×1.0 L). The optical purities of the solid and filtrate were 87% ee and 68% ee respectively (Chiral HPLC Method B). The solid was refluxed in methanol containing 5% of water 12 V (1.2 L) for 20 minutes. The suspension was allowed to cool to room temperature and stirred overnight before the solid was collected by filtration and washed twice with 5% of water in methanol (2×1.0 L). The optical purity of the solid was 94% ee (Chiral HPLC Method B). The solid was refluxed a second time in methanol containing 5% of water (1.2 L). The suspension was allowed to cool to room temperature and stirred overnight before the solid was collected by filtration and washed with 5% of water in methanol (1.2 L). The optical purity of the solid was 97.94% ee (Chiral HPLC Method B). The solid material was dried in vacuum to furnish the diastereomeric salt as white solid (65 g, 33% yield).

Chiral HPLC Method B: e.e.=98.2% (enantiomeric purity=99.1%)

Example 15: (S)-1-(1-(2,3-dihydrobenzofuran-6-yl)ethyl)piperazine

Example 14 was dissolved in water (100 mL) and the resulting solution was basified using 5N NaOH solution (200 mL). The compound was extracted with EtOAc (2×500 mL). The combined organic layer was washed with brine solution (500 mL), dried over anhydrous sodium sulfate and concentrated under vacuum to get the title compound. Yield: 89% (30.5 g, light yellow gum). ¹H NMR (400 MHz, DMSO-d6): δ 7.12; (d, J=7.2 Hz, 1H), 6.73-6.66; (m, 2H), 4.52-4.46; (m, 2H), 3.18-3.11; (m, 4H), 2.70-2.61; (m, 4H), 2.39-2.11; (m, 5H), 1.30-1.12; (m, 3H). LCMS: (Method A) 233.0; (M+H), Rt. 1.63; min, 84.15% (Max). HPLC: (Method A) Rt. 1.64 min, 85.83% (Max). Chiral HPLC Method B: 97.94% (enantiomeric purity=98.9%)

Intermediate 14: 2-(piperazin-1-yl)-6,7-dihydrothiazolo[5,4-c]pyridin-4(5H)-one dihydrochloride

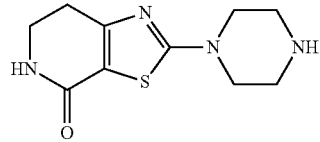 [SMILES: O=C1NCCc2nc(N3CCNCC3)sc21]

Step 1: tert-butyl 3-bromo-2,4-dioxopiperidine-1-carboxylate

To a stirred solution of tert-butyl 2,4-dioxopiperidine-1-carboxylate (1 g, 4.69 mmol) in dry CCl₄ (10 mL), N-bromosuccinimide (0.83 g, 4.69 mmol) was added at 10° C. The reaction mixture was stirred at 10-15° C. for 2 h. It was then evaporated under reduced pressure. Water (10 mL) was added and the desired product was extracted with EtOAc (2×30 mL). The combined organic layer was dried over Na₂SO₄ and concentrated. The resulting crude product was purified by column chromatography, affording the title product. Yield: 99% (1.4 g, off white solid). ¹H NMR (400 MHz, DMSO-d₆): δ 5.50; (s, 1H), 3.74-3.71; (m, 2H), 2.69-2.66; (m, 2H), 1.46; (s, 9H). LCMS: (Method A) 193.8; (M-Boc+H), Rt. 2.93 min, 81.51% (Max).

Step 2: tert-butyl-2-(4-(tert-butoxycarbonyl)piperazin-1-yl)-4-oxo-6,7-dihydrothiazolo[5,4-c]pyridine-5(4H)-carboxylate To a stirred solution of tert-butyl 4-carbamothioylpiperazine-1-carboxylate (1.31 g, 5.36 mmol) in isopropanol (15 mL), tert-butyl 3-bromo-2,4-dioxopiperidine-1-carboxylate obtained in the first step (1.3 g, 4.46 mmol) was added at rt. The reaction mixture was stirred overnight at 90° C. It was cooled down to rt and evaporated under reduced pressure. Water (10 mL) was added and the desired product was extracted with diethyl ether (2×30 mL), dried over $Na_2SO_4$ and concentrated, affording the title product. Yield: 74% (1.42 g, yellow solid). LCMS: (Method A) 239.0; (M-Boc+H), Rt. 0.70 min, 48.39% (Max).

Step 3: 2-(piperazin-1-yl)-6,7-dihydrothiazolo[5,4-c]pyridin-4(5H)-one dihydrochloride To a stirred solution of tert-butyl-2-(4-(tert-butoxycarbonyl)piperazin-1-yl)-4-oxo-6,7-dihydrothiazolo[5,4-c]pyridine-5(4H)-carboxylate obtained in previous step (1.3 g, 2.96 mmol) in 1,4-dioxane (10 mL), HCl in dioxane (4 M solution, 13 mL, 10 V) was added at 0° C. The reaction mixture was stirred for 2 h at rt. It was evaporated and the resulting solid was triturated with EtOAc (3×20 mL) to afford titled compound which was used without further purification. Yield: 99% (crude) (2.25 g, white solid). LCMS: (Method A) 239.0; (M+H), Rt. 0.663 min, 82.012% (Max).

Example 12: 2-(4-(1-(2,3-dihydrobenzofuran-6-yl)ethyl)piperazin-1-yl)-6,7-dihydrothiazolo[5,4-c]pyridin-4(5H)-one

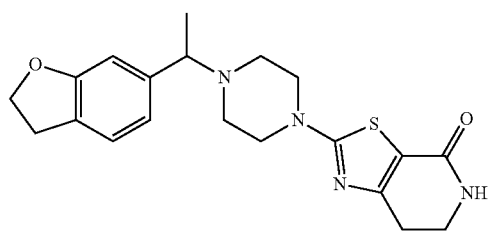 [SMILES: CC(c1ccc2c(c1)OCC2)N1CCN(c2nc3c(s2)C(=O)NCC3)CC1]

To a stirred solution of Intermediate 14 (0.5 g, 1.61 mmol) in DMF (5 mL, 10V), TEA (0.89 mL, 6.4 mmol) and Example 7 (0.44 g, 2.41 mmol) were added at rt and the mixture was stirred at 80° C. for 12 h. It was concentrated under vacuum and resulting crude mixture was purified by MD Autoprep HPLC (Method C) to afford titled compound (off white solid). $^1$H NMR (400 MHz, DMSO-d6): δ 7.29; (s, 1H), 7.16; (d, J=7.2 Hz, 1H), 6.76; (d, J=7.6 Hz, 1H), 6.72; (s, 1H), 4.51; (t, J=8.8 Hz, 2H), 3.46-3.42; (m, 4H), 3.38-3.36; (m, 4H), 3.14; (t, J=8.8 Hz, 2H), 2.69; (t, J=7.2 Hz, 2H), 2.44-2.43; (m, 2H), 1.28; (d, J=6.80 Hz, 3H). LCMS: (Method A) 358.0; (M+H), Rt. 2.324 min, 97.963% (Max). HPLC: (Method A) Rt. 2.279 min, 99.224% (Max).

The S-enantiomer of this compound can be obtained by use of the respective S-intermediate or from its racemate by applying the processes and conditions described in examples 10, 11, 12, 13, 14 and 15.

Example 117: Ethyl 5-(4-(1-(2,3-dihydrobenzofuran-6-yl)ethyl)piperazin-1-yl)-1,3,4-thiadiazole-2-carboxylate

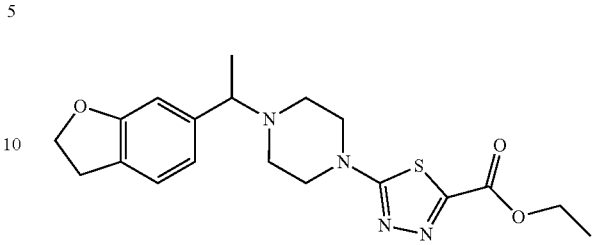

To a stirred solution of ethyl 5-chloro-1,3,4-thiadiazole-2-carboxylate (0.25 g, 1.29 mmol) in dry DMF (2.5 mL), $K_2CO_3$ (0.54 g, 3.89 mmol) and Example 8 (0.59 g, 1.93 mmol) were added at rt. The reaction mixture was stirred overnight at 80° C. It was then concentrated under vacuum. EtOAc (10 mL) was added and the resulting solution was washed with water (10 mL), brine (10 mL), dried over anhydrous $Na_2SO_4$ and concentrated. The crude product was purified by flash chromatography to afford the title compound. Yield: 51% (0.26 g, off white solid). $^1$H NMR (400 MHz, DMSO-d$_6$): δ 7.15; (d, J=7.60 Hz, 1H), 6.75; (d, J=7.60 Hz, 1H), 6.71; (s, 1H), 4.50; (t, J=8.80 Hz, 2H), 4.33; (q, J=6.80 Hz, 2H), 3.54; (t, J=5.20 Hz, 4H), 3.43-3.41; (m, 1H), 3.13; (t, J=8.40 Hz, 2H), 2.45-2.32; (m, 4H), 1.31-1.27; (m, 6H). LCMS: (Method A) 389.2; (M+H), Rt. 2.88 min, 95.7% (Max). HPLC: (Method A) Rt 2.81 min, 96.5% (Max).

The S-enantiomer of this compound can be obtained by use of the respective S-intermediate or from its racemate by applying the processes and conditions described in examples 10, 11, 12, 13, 14 and 15.

Example 118: 5-(4-(1-(2,3-dihydrobenzofuran-6-yl)ethyl)piperazin-1-yl)-N-methyl-1,3,4-thiadiazole-2-carboxamide

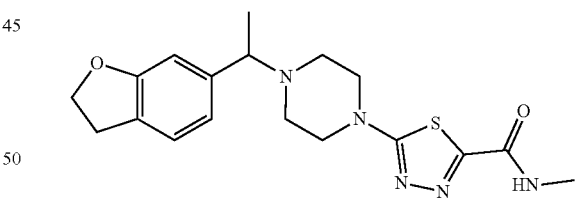

The title compound was synthesized according to the procedure described for Example 98, step 4 and 5, starting from Example 117 (brown thick oil). $^1$H NMR (400 MHz, DMSO-d$_6$): δ 8.74; (q, J=4.8 Hz, 1H), 7.16; (d, J=7.2 Hz, 1H), 6.76; (d, J=1.2 Hz, 1H), 6.72; (s, 1H), 4.51; (t, J=8.40 Hz, 2H), 3.49; (t, J=4.80 Hz, 4H), 3.43-3.41; (m, 1H), 3.14; (t, J=8.80 Hz, 2H), 2.75; (d, J=4.8 Hz, 3H), 2.53-2.51; (m, 2H), 2.46-2.42; (m, 2H), 1.28; (d, J=6.8 Hz, 3H). LCMS: (Method A) 374.0; (M+H), Rt. 2.35 min, 96.4% (Max). HPLC: (Method A) Rt 2.30 min, 98.2% (Max).

The S-enantiomer of this compound can be obtained by use of the respective S-intermediate or from its racemate by applying the processes and conditions described in examples 10, 11, 12, 13, 14 and 15.

Example 41: 5-(4-(1-(benzo[d][1,3]dioxol-5-yl)ethyl)piperazin-1-yl)-1,3,4-thiadiazol-2-amine

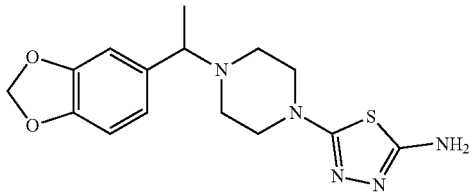 [SMILES: CC(c1ccc2c(c1)OCO2)N1CCN(c2nnc(N)s2)CC1]

The title compound was synthesized following the procedure described for example 117, using Example 2 and 2-amino-5-bromo-1,3,4-thiadiazole. The crude product was purified by recrystallisation. Yield: 81% (2.0 g, off white solid). $^1$H NMR (400 MHz, DMSO-d$_6$): δ 6.88-6.87; (m, 1H), 6.85-6.83; (m, 1H), 6.76-6.73; (m, 1H), 6.47; (s, 2H) 5.99; (s, 2H), 3.40-3.34; (m, 1H), 3.19-3.17; (m, 4H), 2.47-2.43; (m, 2H), 2.40-2.36; (m, 2H), 1.27; (d, J=6.4 Hz, 3H). LCMS: (Method A) 334.0; (M+H), Rt. 1.84 min, 96.5% (Max). HPLC: (Method A) Rt. 1.83 min, 98.2% (Max).

The S-enantiomer of this compound can be obtained by use of the respective

S-intermediate or from its racemate by applying the processes and conditions described in examples 10, 11, 12, 13, 14 and 15.

Example 44: N-(5-(4-(1-(Benzo[d][1,3]dioxol-5-yl)ethyl)piperazin-1-yl)-1,3,4-thiadiazol-2-yl)acetamide

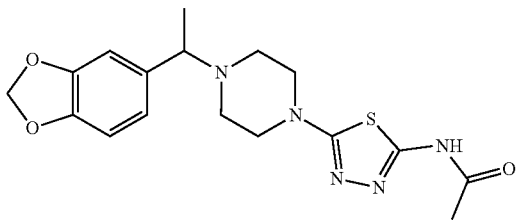 [SMILES: CC(=O)Nc1nnc(N2CCN(C(C)c3ccc4c(c3)OCO4)CC2)s1]

To a stirred solution of Example 41 (0.06 g, 0.7 mmol), diisopropylethylamine (0.4 mL, 0.32 mmol) in dry DCM (4.0 mL), acetic anhydride (0.96 mL, 1.05 mmol) was added at 0° C. and the resulting mixture was stirred for 5 h at rt. The completion of the reaction was monitored by TLC. The reaction mixture was concentrated and the crude products were purified by flash chromatography to afford the title compound (colorless oil). $^1$H NMR (400 MHz, DMSO-d$_6$): δ 12.03; (m, 1H), δ 6.89; (m, 1H), 6.86-6.84; (m, 1H), 6.77-6.75; (m, 1H), 5.99; (m, 2H), 3.41-3.40; (m, 5H), 2.51-2.50; (m, 2H), 2.43-2.40; (m, 2H), 2.10; (s, 3H), 1.28; (d, J=6.8 Hz, 3H). LCMS: (Method A) 376.0; (M+H), Rt. 2.512 min, 96.77% (Max). HPLC: (Method A) Rt. 2.262 min, 98.69% (Max).

The S-enantiomer of this compound can be obtained by use of the respective S-intermediate or from its racemate by applying the processes and conditions described in examples 10, 11, 12, 13, 14 and 15.

Example 68 and Example 69: (R)—N-(5-(4-(1-(benzo[d][1,3]dioxol-5-yl)ethyl)piperazin-1-yl)-1,3,4-thiadiazol-2-yl)acetamide and (S)—N-(5-(4-(1-(benzo[d][1,3]dioxol-5-yl)ethyl)piperazin-1-yl)-1,3,4-thiadiazol-2-yl)acetamide

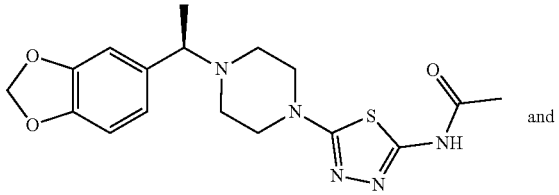
and
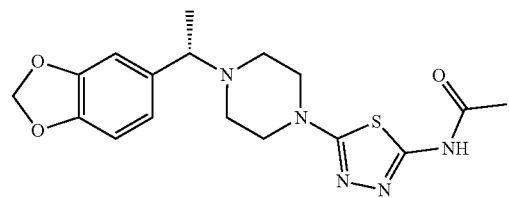

Both enantiomers of Example 44 were separated by SFC using the preparative chiral method PA. The first fraction was collected as Example 68 (off white solid). $^1$H NMR (400 MHz, DMSO-d$_6$): δ 11.66; (br s, 1H), 6.89; (s, 1H), 6.85; (d, J=8.0 Hz, 1H), 6.76; (d, J=8.0 Hz, 1H), 5.99; (m, 2H), 3.42-3.34; (m, 5H), 2.51-2.50; (m, 2H), 2.43-2.33; (m, 2H), 2.09; (s, 3H), 1.27; (d, J=6.4 Hz, 3H). LCMS: (Method A) 376.0; (M+H), Rt. 2.27 min, 97.4% (Max). HPLC:

(Method A) Rt. 2.29 min, 98.2% (Max). Chiral HPLC: (Method D) Rt. 24.02 min, 99.3% (Max). The second fraction was collected as Example 69 (off white solid). $^1$H NMR (400 MHz, DMSO-d$_6$): δ 11.66; (br s, 1H), 6.89; (s, 1H), 6.85; (d, J=8.0 Hz, 1H), 6.76; (dd, J=8.0, 1.2 Hz, 1H), 5.99; (m, 2H), 3.41-3.34; (m, 5H), 2.55-2.47; (m, 2H), 2.43-2.39; (m, 2H), 2.09; (s, 3H), 1.27; (d, J=6.4 Hz, 3H). LCMS: (Method A) 376.0; (M+H), Rt. 2.28 min, 95.8% (Max). HPLC: (Method A) Rt. 2.29 min, 97.1% (Max). Chiral HPLC: (Method D) Rt. 26.57 min, 97.5% (Max).

The S-enantiomer of this compound can also be obtained by use of the respective S-intermediate or from its racemate by applying the processes and conditions described in examples 10, 11, 12, 13, 14 and 15.

Example 65 and Example 66: (R)-2-(4-(1-(benzo[d][1,3]dioxol-5-yl)ethyl)piperazin-1-yl)-N-methylthiazole-5-carboxamide and (S)-2-(4-(1-(benzo[d][1,3]dioxol-5-yl)ethyl)piperazin-1-yl-N-methylthiazole-5-carboxamide

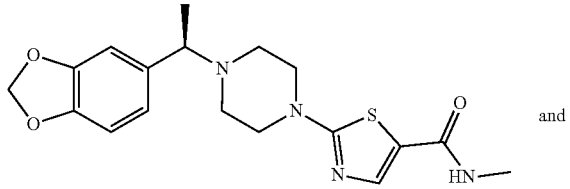
and

-continued

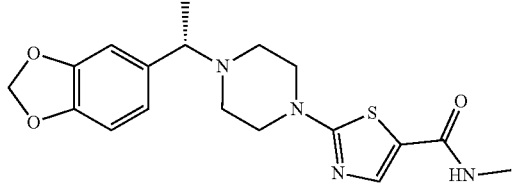

The title compounds were synthesized according to procedures reported in the literature and known by persons skill in the art, starting from Example 2 and ethyl-2-bromothiazole-5-carboxylate. A preferred method of preparation is given below.

Step 1: Ethyl 2-bromothiazole-5-carboxylate

To a stirred solution of ethyl-2-amino thiazole-5-carboxylate (10.0 g, 46.45 mmol, Combi block) in 48% HBr (75 mL), sodium nitrite (4.80 g, 69.68 mmol) in water (50 mL) was added dropwise at 0° C. and the reaction mixture was stirred at 0° C. for 15 min. Copper (I) bromide (6.66 g, 46.45 mmol) in 48% HBr (75 mL) was added dropwise at 0° C. and the reaction mixture was stirred at rt for 4 h. The reaction mixture was diluted with DCM (200 mL) and washed with water (50 mL), brine (50 mL), dried over $Na_2SO_4$ and concentrated under reduced pressure. The crude product was purified by flash chromatography (100% $CHCl_3$) to afford the title compound. Yield: 50.18% (5.5 g, yellow liquid). $^1$H NMR (400 MHz, DMSO-$d_6$): δ8.16; (s, 1H), 4.38; (q, J=7.16 Hz, 2H), 1.40; (t, J=7.12 Hz, 3H). LCMS: (Method A) 235.9; (M+H), Rt. 3.85 min, 98.6% (Max).

Step 2: Ethyl 2-(4-(1-(benzo[d][1,3]dioxol-5-yl)ethyl)piperazin-1-yl)thiazole-5-carboxylate To a stirred solution of Example 5 (1.5 g, 6.40 mmol) in dry DMF (15 mL), ethyl 2-bromothiazole-5-carboxylate (1.96 g, 8.32 mmol) and TEA (3.5 mL, 25.6 mmol) were added at rt and the reaction mixture was stirred at 120° C. for overnight. The reaction mixture was cooled to rt and was diluted with EtOAc. The organic layer was washed with brine (10 mL), water (10 mL), dried over anhydrous $Na_2SO_4$ and concentrated under vacuum. The crude product was purified by column chromatography to afford the title compound (off white solid). $^1$H NMR (400 MHz, DMSO-$d_6$): δ 7.83; (s, 1H), 6.89; (s, 1H), 6.89; (d, J=8.0 Hz, 1H). 6.76; (d, J=8.0 Hz, 1H), 5.99; (s, 2H), 4.19; (q, J=6.8 Hz, 2H), 3.50-3.42; (m, 5H), 2.51-2.46; (m, 2H), 2.44-2.33; (m, 2H), 1.30-1.22; (m, 6H). LCMS: (Method A) 247.2; (M+H), Rt. 3.17 min, 78.6% (Max).

Step 3: 2-(4-(1-(Benzo[d][1,3]dioxol-5-yl)ethyl)piperazin-1-yl)thiazole-5-carboxylic Acid To a stirred solution of ethyl 2-(4-(1-(benzo[d][1,3]dioxol-5-yl)ethyl)piperazin-1-yl)thiazole-5-carboxylate (0.8 g, 2.05 mmol) in dioxane (24 mL), NaOH (2M in water, 3 mL) was added slowly. The reaction mixture was stirred overnight at room temperature. It was then concentrated under vacuum and neutralized with HCl (1.5 N) up to pH=6 and was extracted with DCM (25 mL). The organic layer was washed with water (15 mL), brine (15 mL), dried over anhydrous $Na_2SO_4$ and concentrated under reduced pressure to afford the title compound (off white solid). LCMS: (Method A) 362.0; (M+H), Rt. 2.30 min, 77.6% (Max).

Step 4: (R)-2-(4-(1-(benzo[d][1,3]dioxol-5-yl)ethyl)piperazin-1-yl)-N-methylthiazole-5-carboxamide and (S)-2-(4-(1-(benzo[d][1,3]dioxol-5-yl)ethyl)piperazin-1-yl)-N-methylthiazole-5-carboxamide To a stirred solution of 2-(4-(1-(benzo[d][1,3]dioxol-5-yl)ethyl)piperazin-1-yl)thiazole-5-carboxylic acid (500 mg, 1.33 mmol) in DMF (10 mL), DIPEA (0.7 mL, 3.99 mmol), methyl amine (2 M in THF, 1 mL, 2.00 mmo) and HATU (607 mg, 1.60 mmol) were added at 0° C. The reaction mixture was stirred at room temperature overnight. The reaction mixture was concentrated under vacuum and diluted with DCM. It was washed with water, brine and dried over anhydrous $Na_2SO_4$. The crude mixture was purified by flash chromatography followed by chiral preparative HPLC (Method PF) to seperate enantiomers. The first fraction was concentrated to give Example 65 (white solid). $^1$H NMR (400 MHz, DMSO-$d_6$): δ 8.16; (d, J=4.4 Hz, 1H), 7.72; (s, 1H), 6.89; (s, 1H), 6.85; (d, J=7.6 Hz, 1H), 6.76; (d, J=8.0 Hz, 1H), 5.99; (br s, 2H), 3.43-3.42 (m, 5H), 2.69; (d, J=4.4 Hz, 3H), 2.47-2.33; (m, 4H), 1.28; (d, J=6.4 Hz, 3H). LCMS: (Method A) 375.0; (M+H), Rt. 2.23 min, 99.0% (Max). HPLC: (Method A) Rt. 2.19 min, 99.6% (Max). Chiral HPLC: (Method D) Rt. 15.48 min, 98.91%.

The second fraction was concentrated to give Example 66 (white solid). $^1$H NMR (400 MHz, DMSO-$d_6$): δ 8.16; (q, J=4.8 Hz, 1H), 7.72; (s, 1H), 6.90; (s, 1H), 6.85; (d, J=8.0 Hz, 1H), 6.76; (d, J=8.0 Hz, 1H), 5.99; (br s, 2H), 3.43-3.41; (m, 5H), 2.69; (d, J=4.8 Hz, 3H), 2.48-2.39; (m, 4H), 1.28; (d, J=6.8 Hz, 3H). LCMS: (Method A) 375.0; (M+H), Rt. 2.23 min, 97.4% (Max). HPLC: (Method A) Rt. 2.19 min, 96.9% (Max). Chiral HPLC: (Method D) Rt. 18.44 min, 100.00%

The S-enantiomer of this compound can also be obtained by use of the respective S-intermediate or from its racemate by applying the processes and conditions described in examples 10, 11, 12, 13, 14 and 15.

Example 70: 2-(4-(1-(Benzol[d][1,3]dioxol-5-yl)ethyl)piperazin-1-yl)pyrimidin-5-amine

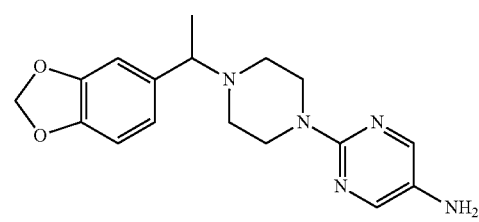 [SMILES: CC(c1ccc2c(c1)OCO2)N1CCN(c2ncc(N)cn2)CC1]

Step 1: 2-(4-(1-(Benzo[d][1,3]dioxol-5-yl)ethyl)piperazin-1-yl)-4-nitropyrimidine To a stirred solution of Example 2 (1 g, 4.2 mmol) in dry DMF (10 mL), $Et_3N$ (2.3 mL, 16.8 mmol) and 2-chloro-5-nitropyrimidine (0.74 g, 4.6 mmol) were added at rt and the resulting mixture was stirred at 120° C. for 20 h. It was diluted with water and extracted with EtOAc. The organic layer was dried over anhydrous $Na_2SO_4$ and concentrated under vacuum. The resulting crude product was purified by flash chromatography to give the title compound (yellow solid). $^1$H NMR (400 MHz, DMSO-d$_6$): δ 9.08; (s, 2H), 6.92; (s, 1H), 6.85-6.83; (m, 1H), 6.77; (s, 1H), 5.98; (m, 2H), 3.89; (s, 4H), 3.50; (s, 1H), 2.45-2.44; (m, 4H), 1.30; (br s, 3H). LCMS: (Method A) 358.0; (M+H), Rt. 3.00 min, 94.23% (Max).

Step 2: 2-(4-(1-(Benzo[d][1,3]dioxol-5-yl)ethyl) piperazin-1-yl)pyrimidin-5-amine To a stirred solution of 2-(4-(1-(benzo[d][1,3]dioxol-5-yl)ethyl)piperazin-1-yl)-4-nitropyrimidine (0.70 g, 1.9 mmol) in methanol (14 mL), Pd/C (0.07 g, 10% w/w) was added at rt and the resulting mixture was stirred under hydrogen atmosphere (5 kg/cm$^2$) overnight at rt. The reaction mixture was filtered through celite and washed with methanol. The filtrate was dried over anhydrous Na$_2$SO$_4$ and concentrated under vacuum. The crude product was purified by flash chromatography to afford the title compound (yellow solid). $^1$H NMR (400 MHz, DMSO-d$_6$): δ 7.86; (s, 2H), 6.88; (s, 1H), 6.84; (d, J=8.0 Hz, 1H), 6.75; (d, J=7.6 Hz, 1H), 6.46; (s, 2H), 5.98; (m, 2H), 3.48-3.45; (m, 4H), 2.43-2.42; (m, 2H), 2.34-2.31; (m, 2H), 1.27; (d, J=6.8 Hz, 3H). LCMS: (Method A) 328.2; (M+H), Rt. 1.91 min, 96.83% (Max). HPLC: (Method A) Rt. 1.88 min, 95.85% (Max).

The S-enantiomer of this compound can be obtained by use of the respective S-intermediate or from its racemate by applying the processes and conditions described in examples 10, 11, 12, 13, 14 and 15.

Example 72: N-(2-(4-(1-(benzo[d][1,3]dioxol-5-yl) ethyl)piperazin-1-yl)pyrimidin-5-yl)acetamide

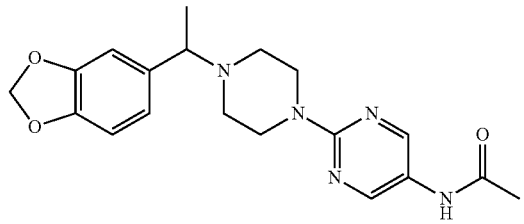 [SMILES: CC(=O)Nc1cnc(N2CCN(C(C)c3ccc4c(c3)OCO4)CC2)nc1]

To a stirred solution of Example 70 (180 mg, 0.54 mmol) in dry pyridine (1.35 mL), acetic anhydride (0.06 mL, 0.65 mmol) was added at room temperature and the resulting mixture was stirred at 50° C. overnight. It was diluted with ethyl acetate (100 mL) and washed with HCl (1.5 N), water, brine and dried over Na$_2$SO$_4$. After evaporation of the solvents, the crude product was purified by flash chromatography to afford the title compound (yellow solid). $^1$H NMR (400 MHz, DMSO-d$_6$): δ 9.82; (s, 1H), 8.46; (d, J=0.4 Hz, 2H), 6.89; (s, 1H), 6.84; (d, J=7.6 Hz, 1H), 6.76; (d, J=7.6 Hz, 1H), 5.98; (m, 2H), 3.64-3.62; (m, 4H), 3.36-3.34; (m, 1H), 2.45-2.32; (m, 4H), 2.00; (s, 3H), 1.25; (d, J=6.8 Hz, 3H). LCMS: (Method A) 370.2; (M+H), Rt. 2.30 min, 94.42% (Max). HPLC: (Method A) Rt. 2.22 min, 95.29% (Max).

The S-enantiomer of this compound can be obtained by use of the respective S-intermediate or from its racemate by applying the processes and conditions described in examples 10, 11, 12, 13, 14 and 15.

Example 77 and Example 78: (R)—N-(2-(4-(1-(benzo[d][1,3]dioxol-5-yl)ethyl)piperazin-1-yl)pyrimidin-5-yl)acetamide and (S)—N-(2-(4-(1-(benzo[d][1,3]dioxol-5-yl)ethyl)piperazin-1-yl)pyrimidin-5-yl)acetamide

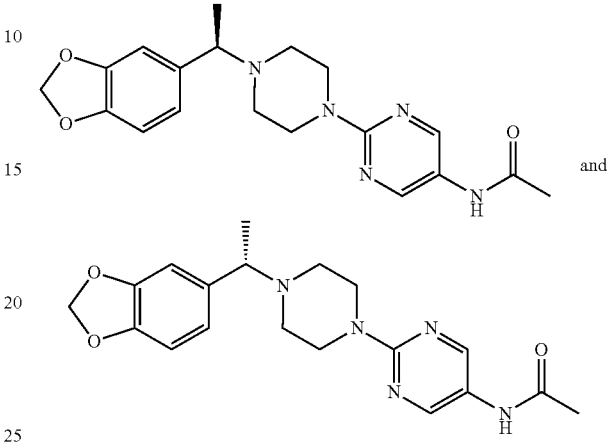

Example 72 was submitted to chiral preparative HPLC (Method PD). The first eluting fraction was concentrated, affording Example 77 (pale yellow solid).

$^1$H NMR (400 MHz, DMSO-d6): δ 9.81; (s, 1H), 8.46; (s, 2H), 6.89; (s, 1H), 6.84; (d, J=8.0 Hz, 1H), 6.76; (d, J=8.0 Hz, 1H), 5.98; (m, 2H), 3.63; (t, J=4.8 Hz, 4H), 3.31; (s, 1H), 2.44-2.33; (m, 4H), 2.00; (s, 3H), 1.26; (d, J=6.0 Hz, 3H).

LCMS: (Method A) 370.2; (M+H), Rt. 2.33 min, 99.5% (Max). HPLC: (Method A) Rt. 2.24 min, 99.7% (Max). Chiral HPLC: (Method F) Rt. 31.24 min, 99.05%. The second eluting fraction was concentrated, affording Example 78 (pale yellow solid). 1H NMR (400 MHz, DMSO-d$_6$): δ 9.81; (s, 1H), 8.46; (s, 2H), 6.89; (s, 1H), 6.84; (d, J=8.0 Hz, 1H), 6.76; (d, J=8.0 Hz, 1H), 5.98; (m, 2H), 3.63; (t, J=4.8 Hz, 4H), 3.31; (s, 1H), 2.41-2.32; (m, 4H), 2.00; (s, 3H), 1.26; (d, J=6.0 Hz, 3H). LCMS: (Method A) 370.2; (M+H), Rt. 2.31 min, 99.5% (Max). HPLC: (Method A) Rt. 2.25 min, 99.8% (Max). Chiral HPLC: (Method F) Rt. 21.26 min, 100.00%.

The S-enantiomer of this compound can also be obtained by use of the respective S-intermediate or from its racemate by applying the processes and conditions described in examples 10, 11, 12, 13, 14 and 15.

Example 98: 2-(4-(1-(Benzo[d][1,3]dioxol-5-yl)ethyl) piperazin-1-yl)-N-methylpyrimidine-5-carboxamide

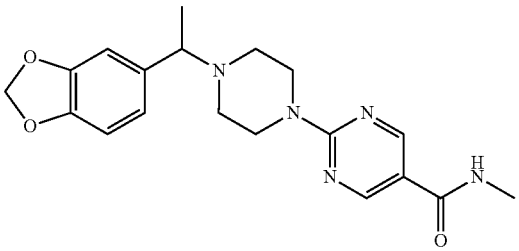 [SMILES: CNC(=O)c1cnc(N2CCN(C(C)c3ccc4c(c3)OCO4)CC2)nc1]

Step 1: Ethyl 2-(methylthio)pyrimidine-5-carboxylate

To a stirred solution of ethyl-4-chloro-(2-methyl thio pyrimidine) 5-carboxylate (10 g, 42.9 mmol) in THF/water (8:2, 100 mL), zinc powder (14.0 g, 0.21 mmol) followed by t-BuOH (2 mL) were added and the resulting mixture was heated at 90° C. fo overnight. The reaction completion was monitored by LCMS. The mixture was filtered through celite and evaporated under vaccum. The crude product was dissolved in dichloromethane (100 mL), washed with water (50 mL) and dried over $Na_2SO_4$. After evaporation of the solvents, the crude product was purified by MD Autoprep (Method B) (colorless liquid). $^1$H NMR (400 MHz, DMSO-$d_6$): 9.03; (s, 2H), 4.35; (q, J=7.1 Hz, 2H), 2.58; (s, 3H), 1.33; (t, J=7.08 Hz, 3H). LCMS: (Method A) 199.0; (M+H), Rt. 3.50 min, 99.7% (Max).

Step 2: Ethyl 2-(methylsulfonyl)pyrimidine-5-carboxylate

To a stirred solution of ethyl 2-(methylthio)pyrimidine-5-carboxylate (2.8 g, 14.2 mmol) in tetrahydrofuran at 0° C., 3-chloroperbenzoic acid (7.8 g, 60.7 mmol, spectrochem) was added and the resulting solution was stirred at rt for 3 h. It was concentrated. DCM was added and was washed with water (25 mL) and 10% sodium bicarbonate solution (20 mL) and dried over $Na_2SO_4$. After evaporation of the solvents, the crude product was purified by flash chromatography to afford the titled product. Yield: 50.7% (1.65 g, off white solid). $^1$H NMR (400 MHz, DMSO-$d_6$): 9.48; (s, 2H), 4.43; (q, J=7.0 Hz, 2H), 3.48; (s, 3H), 1.37; (t, J=7.1 Hz, 3H). LCMS: (Method A) 230.9; (M+H), Rt. 2.33 min, 97.48% (Max).

Step 3: Ethyl 2-(4-(1-(benzo[d][1,3]dioxol-5-yl)ethyl)piperazin-1-yl)pyrimidine-5-carboxylate To a stirred solution of Example 2 (1.87 g, 6.94 mmol) in dry acetonitrile, potassium carbonate (2.87 g, 20.8 mmol, spectrochem) and ethyl 2-(methylsulfonyl)pyrimidine-5-carboxylate were added and the resulting mixture was at rt for 12 h. It was filtered through celite and concentrated. Dichloromethane (25 mL) was added and the solution was washed with water, brine and dried over $Na_2SO_4$. After evaporation of the solvents, the crude product was purified by flash column chromatography to afford the title compound (white solid). $^1$H NMR (400 MHz, DMSO-$d_6$): 8.74; (s, 2H), 6.85; (t, J=7.8 Hz, 2H), 6.75; (d, J=7.8 Hz, 1H), 5.98; (s, 2H), 4.25; (q, J=6.8 Hz, 2H), 3.81; (s, 4H), 3.32; (s, 1H), 2.37-2.42; (m, 4H), 1.28; (d, J=6.6 Hz, 6H). LCMS: (Method A) 385.2; (M+H), Rt. 3.22 min, 98.88% (Max).

Step 4: Lithium 2-(4-(1-(benzo[d][1,3]dioxol-5-yl)ethyl)piperazin-1-yl)pyrimidine-5-carboxylate To a stirred solution of ethyl 2-(4-(1-(benzo[d][1,3]dioxol-5-yl)ethyl)piperazin-1-yl)pyrimidine-5-carboxylate (0.9 g, 2.34 mmol) in MeOH (2 mL), THF (7 mL) and water (1 mL) mixture, lithium hydroxide (0.24 g, 5.85 mmol, spectrochem) was added at 0° C. The resulting mixture was stirred at rt for 12 h. It was concentrated and the crude product was used without further purification. Yield: 90% (0.52 g, off white solid). LCMS: (Method A) 357.0; (M+H), Rt. 2.38 min, 99.21% (Max).

Step 5: 2-(4-(1-(Benzo[d][1,3]dioxol-5-yl)ethyl)piperazin-1-yl)-N-methylpyrimidine-5-carboxamide To a stirred solution of lithium 2-(4-(1-(benzo[d][1,3]dioxol-5-yl)ethyl)piperazin-1-yl)pyrimidine-5-carboxylate (300 mg, 0.82 mmol) in dry DMF (5 mL), methyl amine (0.09 mL, 0.988 mmol, 2M in THF), DIPEA (0.45 mL, 2.47 mmol) and HATU (471 mg, 1.29 mmol) were added and the resulting mixture was stirred at rt for 12 h. It was concentrated under vacuum and the crude product was diluted with DCM (20 mL), washed with water (15 mL) and dried over anhydrous $Na_2SO_4$. After evaporation of the solvents, the crude product was purified by MD Autoprep (Method B) to give the title compound (off white solid). $^1$H NMR (400 MHz, DMSO-$d_6$): δ 8.71; (s, 2H), 8.29; (q, J=4.4 Hz, 1H), 6.90; (d, J=1.6 Hz, 1H), 6.84; (d, J=7.6 Hz, 1H), 6.75; (dd, J=8.0, 1.2 Hz, 1H), 5.98; (m, 2H), 3.78-3.76; (m, 4H), 3.39; (q, J=6.4 Hz, 1H), 2.74; (d, J=4.8 Hz, 3H), 2.45-2.42; (m, 2H), 2.37-2.32; (m, 2H), 1.28; (d, J=6.4 Hz, 3H).

LCMS: (Method A) 370.2; (M+H), Rt. 2.24 min, 97.69% (Max). HPLC: (Method A) Rt. 2.19 min, 99.52% (Max).

The S-enantiomer of this compound can be obtained by use of the respective S-intermediate or from its racemate by applying the processes and conditions described in examples 10, 11, 12, 13, 14 and 15.

Example 134: (S) 2-(4-(1-(benzo[d][1,3]dioxol-5-yl)ethyl)piperazin-1-yl)-N-methylpyrimidine-5-carboxamide

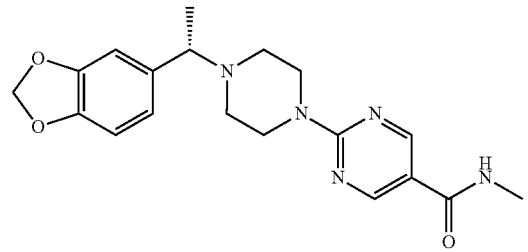 [SMILES: CNC(=O)c1cnc(N2CCN([C@@H](C)c3ccc4c(c3)OCO4)CC2)nc1]

Step 1: Ethyl (S)-2-(4-(1-(benzo[d][1,3]dioxol-5-yl)ethyl)piperazin-1-yl)pyrimidine-5-carboxylate To a stirred solution of Example 13 (1.87 g, 6.94 mmol) in dry acetonitrile (10 mL), potassium carbonate (2.87 g, 20.8 mmol, Spectrochem) and ethyl 2-(methylsulfonyl)pyrimidine-5-carboxylate (1.6 g, 6.94 mmol, synthesis described in Example 98, steps, 1 and 2) were added. The resulting mixture was stirred at rt for 3 h. It was then filtered through celite and concentrated. The crude product was diluted with dichloromethane (25 mL), washed with water and dried over anhydrous $Na_2SO_4$. After evaporation of the solvent, the crude product was purified by flash column chromatography to afford the title compound (white solid). $^1$H NMR (400 MHz, DMSO-$d_6$): δ 8.74; (s, 1H), 6.78-6.72; (m, 2H), 5.97; (s, 1H), 4.38-4.36; (m, 1H), 3.81; (s, 2H), 2.37-2.47; (m, 9H), 1.26; (d, J=2.84 Hz, 3H), LCMS: (Method A) 385.2; (M+H), Rt. 3.22 min, 98.6% (Max).

Step 2: Lithium (S)-2-(4-(1-(benzo[d][1,3]dioxol-5-yl)ethyl)piperazin-1-yl)pyrimidine-5-carboxylate To a stirred solution of ethyl (S)-2-(4-(1-(benzo[d][1,3]dioxol-5-yl)ethyl)piperazin-1-yl)pyrimidine-5-carboxylate (1.6 g, 17.5 mmol) in a mixture of MeOH (2 mL), THF (7 mL) and water (1 mL), lithium hydroxide (0.431 g, 5.20 mmol, Spectrochem) was added at 0° C. and the resulting mixture was stirred at rt for 12 h. It was concentrated and the resulting product was taken for next step without any further purification. Yield: 96% (0.61 g, off white solid). $^1$H NMR (400 MHz, DMSO-$d_6$): δ 8.61; (s, 1H), 6.81-6.88; (m, 4H), 5.97; (d, J=1.8 Hz, 2H), 3.68; (d, J=6.2 Hz, 2H), 3.22-3.21; (m, 1H), 2.28-2.35; (m, 6H), 1.26; (d, J=8.9 Hz, 3H), LCMS: (Method A) 357.0; (M+H), Rt. 2.41 min, 97.1% (Max)

Step 3: (S) 2-(4-(1-(benzo[d][1,3]dioxol-5-yl)ethyl)piperazin-1-yl)-N-methylpyrimidine-5-carboxamide To a stirred solution of lithium (S)-2-(4-(1-(benzo[d][1,3]dioxol-5-yl)ethyl)piperazin-1-yl)pyrimidine-5-carboxylate (0.3 g, 0.82 mmol) in dry DCM (10 mL), triethylamine (0.34 mL) and methylamine in THF (2 M, 1.6 mL, 3.32 mmol) were added at 0° C. The reaction mixture was stirred at rt for 1 h. The reaction progression was monitored by TLC. After completion of the reaction, the mixture was diluted with 10% sodium bicarbonate solution (10 mL) and extracted with DCM (20 mL). The organic layer was dried over $Na_2SO_4$ and evaporated to dryness. The crude product was purified by flash column chromatography. Yield: 56% (0.17 g, off white solid). $^1$H NMR (400 MHz, DMSO-$d_6$): δ 8.71; (s, 2H), 8.28; (d, J=4.8 Hz, 1H), 6.90-6.83; (m, 2H), 6.77-6.75; (m, 1H), 5.98; (d, J=2.0 Hz, 2H), 3.77; (t, J=4.8 Hz, 4H), 3.41-3.38; (m, 1H), 2.74; (d, J=4.4 Hz, 3H), 2.38-2.33; (m, 4H), 1.28; (d, J=6.8 Hz, 3H). LCMS: (Method A) 370.2; (M+H), Rt. 2.21 min, 98.9% (Max). HPLC:
(Method A) Rt. 2.18 min, 99.3% (Max). Chiral HPLC: (Method G) Rt. 5.51 min, 100.00%.

The S-enantiomer of this compound can also be obtained from its racemate by applying the processes and conditions described in examples 10, 11, 12, 13, 14 and 15.

The invention claimed is:

1. A process for the separation of the enantiomers of a compound of formula I

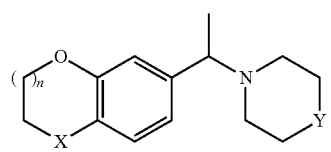

(I)

wherein
X denotes O or $CH_2$,
Y is NH or N-PG,
PG denotes a protective group selected from a carbobenzyloxy (Cbz), p-methoxybenzyl carbonyl (Moz or MeOZ) group, tert-butyloxycarbonyl (BOC) group, 9-fluorenylmethyloxycarbonyl (FMOC) group, alkanoyl group, such as the acetyl (Ac) group, benzoyl (Bz) group, benzyl (Bn) group, carbamate group, p-methoxybenzyl (PMB), 4-dimethoxybenzyl (DMPM), p-methoxyphenyl (PMP) group, or arylsulfonyl group,
and
n denotes 0 or 1,
comprising the steps of:
a) contacting the respective racemate or other enantiomeric mixture of the respective compound of formula I with a chiral, non-racemic acid in a suitable solvent, wherein the chiral, non-racemic acid is selected from (1R or 1S)-10-camphorsulfonic acid, (1R or 1S)-3-bromocamphor-10-sulfonic acid, (D or L)-tartaric acid and substituted analogues such as (D or L)-diacetyltartaric acid, (D or L)-dibenzoyl tartaric acid, (D or L)-di-O,O'-p-toluoyl-tartaric acid, (D or L)-di-O,O'-o-toluoyl-tartaric acid, (R or S)-1,1"-binaphthyl-2,2"-diyl-hydrogenphosphate, (D or L)-N-acetyl-phenylalanine, (D or L)-acetylmandelic acid, (R or S)-cyclohexylphenylglycolic acid, (S)-camphanic acid, (R or S)-2-pyrrolidone-5-carboxylic acid, naproxen, ibuprofen; (D or L)-malic acid, L-lactic acid, (R or S)-3-hydroxybutyric acid, hyodeoxycholic acid, (R or S)-mandelic acid, (R or S)-Me-mandelic acid, (R or S)-4-bromo-mandelic acid, (R or S)-4-chloro-mandelic acid or (R or S)-phenylsuccinic acid, or suitable N-protected amino acids, or substituted (D or L)-tartaric acids;
b) optionally heating the mixture obtained under step a) and allowing the mixture to cool to room temperature;
c) separating the formed crystals from the solution;
d) optionally liberating the free base of the respective enantiomer of formula I from the formed crystals obtained under c) by treatment with a base.

2. The process according to claim 1, wherein the compound of formula I is the racemate or other enantiomeric mixture of compound (I') or the racemate or other enantiomeric mixture of compound (I"):

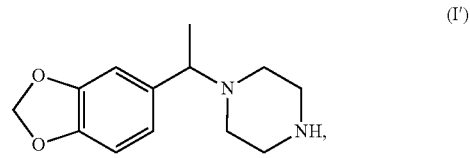

(I')

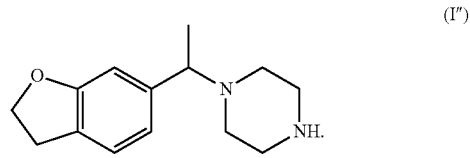

(I")

3. The process according to claim 1, wherein the chiral acid is selected from (S)-Me-mandelic acid, (S)-4-bromo-mandelic acid, (S)-4-chloro-mandelic acid (S)-phenyl succinic acid, dibenzoyl-D-tartaric acid, D-(+)-di-toluoyltartaric acid, D-tartaric acid and di-p-anisoyl-(D)-tartaric acid.

4. The process according to claim 2, wherein the chiral acid is selected from (S)-Me-mandelic acid, (S)-4-bromo-mandelic acid, (S)-4-chloro-mandelic acid (S)-phenyl succinic acid, dibenzoyl-D-tartaric acid, D-(+)-di-toluoyltartaric acid, D-tartaric acid and di-p-anisoyl-(D)-tartaric acid.

5. The process according to claim 3, wherein the chiral acid is employed in a molar ratio to the compounds of formula I of between about 1 to 2 (i.e. about 0.5 equivalents based on the compounds of formula I) and about 3 to 1 (i.e. about 3 equivalents).

6. The process according to claim 4, wherein the chiral acid is employed in a molar ratio to the compounds of formula I of between about 1 to 2 (i.e. about 0.5 equivalents based on the compounds of formula I) and about 3 to 1 (i.e. about 3 equivalents).

7. The process according to claim 5, wherein the solvent is selected from $H_2O$, MeCN, about 2 to about 50% $H_2O$ in EtOH, EtOH, 2 to 50% H₂O in MeOH, MeOH, 2 to 50% H₂O in IPA, IPA, 2 to 50% MeOH in MEK, MEK, 2 to 50% MeOH in iPrOAc, iPrOAc and dioxane.

8. The process according to claim 6, wherein the solvent is selected from H₂O, MeCN, about 2 to about 50% H₂O in EtOH, EtOH, 2 to 50% H₂O in MeOH, MeOH, 2 to 50% H₂O in IPA, IPA, 2 to 50% MeOH in MEK, MEK, 2 to 50% MeOH in iPrOAc, iPrOAc and dioxane.

9. A free base of a compound of formula II

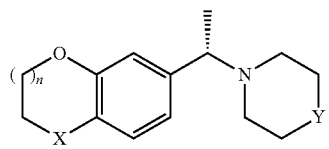

(II)

wherein
X denotes O or CH₂,
Y is NH or N-PG,
PG denotes a protective group selected from a carbobenzyloxy (Cbz), p-methoxybenzyl carbonyl (Moz or MeOZ) group, tert-butyloxycarbonyl (BOC) group, 9-fluorenylmethyloxycarbonyl (FMOC) group, alkanoyl group, such as the acetyl (Ac) group, benzoyl (Bz) group, benzyl (Bn) group, carbamate group, p-methoxybenzyl (PMB), 4-dimethoxybenzyl (DMPM), p-methoxyphenyl (PMP) group, or benzylsulfonyl group, and
n denotes 0.

10. The free base of a compound of formula II of claim 9, wherein the compound is (S)-1-(1-(Benzo[d][1,3]dioxol-5-yl)ethyl)piperazine.

11. The free base of a compound of formula II of claim 9, wherein the compound is (S)-1-(1-(2,3-dihydrobenzofuran-6-yl)ethyl)piperazine.

12. The free base of a compound of formula II of claim 9, wherein the compound is racemic 1-(1-(2,3-dihydrobenzofuran-6-yl)ethyl)piperazine.

13. A salt of a compound of formula II

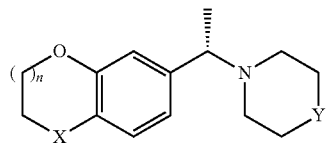

(II)

wherein
X denotes O or CH₂,
Y is NH or N-PG,
PG denotes a protective group
and
n denotes 0 or 1, with an acid selected from (S)-Me-mandelic acid, (S)-4-bromo-mandelic acid, (S)-4-chloro-mandelic acid, (S)-phenylsuccinic acid, dibenzoyl-D-tartaric acid, D-(+)-di-toluoyltartaric acid, D-tartaric acid and di-p-anisoyl-(D)-tartaric acid.

14. The salt of a compound of formula II of claim 13, wherein the compound is (S)-1-(1-(Benzo[d][1,3]dioxol-5-yl)ethyl)piperazine and the acid is selected from (S)-Me-mandelic acid, (S)-4-bromo-mandelic acid, (S)-4-chloro-mandelic acid, (S)-phenylsuccinic acid, dibenzoyl-D-tartaric acid, D-(+)-di-toluoyltartaric acid, D-tartaric acid and di-p-anisoyl-(D)-tartaric acid.

15. The salt of a compound of formula II of claim 13, wherein the compound is (S)-1-(1-(2,3-dihydrobenzo[b][1,4]dioxin-6-yl)ethyl)piperazine and the acid is selected from (S)-Me-mandelic acid, (S)-4-bromo-mandelic acid, (S)-4-chloro-mandelic acid, (S)-phenylsuccinic acid, dibenzoyl-D-tartaric acid, D-(+)-di-toluoyltartaric acid, D-tartaric acid and di-p-anisoyl-(D)-tartaric acid.

16. The salt of a compound of formula II of claim 13, wherein the compound is (S)-1-(1-(2,3-dihydrobenzofuran-6-yl)ethyl)piperazine and the acid is selected from (S)-Me-mandelic acid, (S)-4-bromo-mandelic acid, (S)-4-chloro-mandelic acid, (S)-phenyl succinic acid, dibenzoyl-D-tartaric acid, D-(+)-di-toluoyltartaric acid, D-tartaric acid and di-p-anisoyl-(D)-tartaric acid.

17. The salt according to claim 13, wherein the molar ratio between the piperazine derivative and the acid is 1 to 1.

18. The salt according to claim 14, wherein the molar ratio between the piperazine derivative and the acid is 1 to 1.

19. The salt according to claim 15, wherein the molar ratio between the piperazine derivative and the acid is 1 to 1.

20. The salt according to claim 16, wherein the molar ratio between the piperazine derivative and the acid is 1 to 1.

* * * * *